US008106051B2

(12) United States Patent
Yamamori et al.

(10) Patent No.: US 8,106,051 B2
(45) Date of Patent: Jan. 31, 2012

(54) UTILITIES OF AMIDE COMPOUNDS

(75) Inventors: Teruo Yamamori, Takarazuka (JP); Kiyoshi Nagata, Osaka (JP); Natsuki Ishizuka, Osaka (JP); Katsunori Sakai, Osaka (JP)

(73) Assignee: Shionogi & Co., Ltd., Osaka (JP)

( * ) Notice: Subject to any disclaimer, the term of this patent is extended or adjusted under 35 U.S.C. 154(b) by 532 days.

(21) Appl. No.: 12/081,662

(22) Filed: Apr. 18, 2008

(65) Prior Publication Data

US 2008/0221112 A1 Sep. 11, 2008

Related U.S. Application Data

(62) Division of application No. 10/489,333, filed as application No. PCT/JP01/07980 on Sep. 14, 2001, now Pat. No. 7,429,593.

(51) Int. Cl.
*A01N 43/58* (2006.01)
*A01N 43/60* (2006.01)
*A61K 31/50* (2006.01)
*A61K 31/495* (2006.01)

(52) U.S. Cl. ..................... 514/249
(58) Field of Classification Search .......... None
See application file for complete search history.

(56) References Cited

U.S. PATENT DOCUMENTS

| 3,873,545 | A | 3/1975 | Osselaere et al. |
| 5,399,585 | A | 3/1995 | Alig et al. |
| 5,712,294 | A | 1/1998 | Robert et al. |
| 5,760,066 | A | 6/1998 | Tang |
| 5,843,947 | A | 12/1998 | Robert et al. |
| 6,060,494 | A | 5/2000 | Faasch et al. |
| 2004/0235888 | A1 | 11/2004 | Yamamori et al. |

FOREIGN PATENT DOCUMENTS

| EP | 0515684 | 12/1992 |
| EP | 0 528 146 | 2/1993 |
| EP | 0 718 285 | 6/1996 |
| EP | 0 903 345 | 3/1999 |
| EP | 0 974 573 | 1/2000 |
| EP | 0 987 256 | 3/2000 |
| GB | 2 327 675 | 2/1999 |
| JP | 38-21085 | 10/1963 |
| JP | 57-131719 | 8/1982 |
| JP | 2-235853 | 9/1990 |
| JP | 3-014568 | 1/1991 |
| JP | 3-65243 | 3/1991 |
| JP | 04-128284 | 4/1992 |
| JP | 4-253974 | 9/1992 |
| JP | 6-041118 | 2/1994 |
| JP | 7-130573 | 5/1995 |
| JP | 7-330764 | 12/1995 |
| JP | 9-227371 | 9/1997 |
| JP | 10-29979 | 2/1998 |
| JP | 10-245357 | 9/1998 |
| JP | 11-147874 | 6/1999 |
| JP | 11-158133 | 6/1999 |
| JP | 11-171848 | 6/1999 |
| JP | 11-302254 | 11/1999 |
| JP | 2000-302793 | 10/2000 |
| JP | 2001-139550 | 5/2001 |
| JP | 2001-233767 | 8/2001 |
| WO | 91/11994 | 8/1991 |
| WO | 97/09048 | 3/1997 |
| WO | 98/02412 | 1/1998 |
| WO | 98/17267 | 4/1998 |
| WO | 99/07382 | 2/1999 |
| WO | 99/07669 | 2/1999 |
| WO | 99/24404 | 5/1999 |

OTHER PUBLICATIONS http://en.wikipedia.org/wiki/Dyslipidemia; last accessed Nov. 29, 2010.*
Wolff et. al., "Burger's Medicinal Chemistry and Drug Discovery," 5th Ed. Part 1, pp. 975-977 (1995).*
Dorwald F. A. Side Reactions in Organic Synthesis, 2005, Wiley: VCH, Weinheim p. IX of Preface.*
Banker, et. al., Modern Pharmaceuticals, (1996); p. 596.*
Vippagunta et. al. Advanced Drug Delivery Reviews 48 (2001) 3-26.*
Mndzhoyan and Afrikyan, "Amides of the Pyridine and Thiazole Series" Izvest. Akad, Nauk Armayn. S.S.R., Ser. Khim. Nauk, vol. 10, pp. 143-156 (1957). As Abstracted by Caplus (STN).
Mndzhoyan and Afrikyan, "Amides of the Pyridine and Thiazole Series" Izvest. Akad, Nauk Armayn. S.S.R., Ser. Khim. Nauk, vol. 10, pp. 143-156 (1957). With English Translation.
Robert et al., "Synthesis and Anti-inflammatory Activity of Polyazaheterocyclic Derivatives of 6-Amino-2,4-lutidine and Their Precursors", Arzneitmittel Forschung, vol. 47(5), pp. 635-642, (1997) As Abstracted by Caplus.
Calvert et al., "Synthetic and Mechanistic Investigations of the Reductive Electrochemical Polymerization of Vinyl-Containing Complexes of Iron(II), Ruthenium(II) and Osmium(II)" Inorganic Chemistry, vol. 22(15), pp. 2151-2162, (1983).

(Continued)

*Primary Examiner* — Jeffrey Murray
(74) *Attorney, Agent, or Firm* — Wenderoth Lind & Ponack, L.L.P.

(57) ABSTRACT

Compounds having an activity to enhance the expression of apoAI are provided, which are used as medicaments.
Compounds of formula (I):

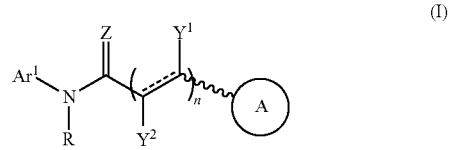

in which ring A and $Ar^1$ are independently a monocyclic or bicyclic aromatic carbocyclic group or aromatic heterocyclic group, each of which may be optionally substituted, or the like; R is a hydrogen or the like; Z is oxygen or the like; $Y^1$ and $Y^2$ are a hydrogen, a lower alkyl, or the like; n is an integer of 0 to 2; the broken line is the presence or absence of a bond; and the wavy line represents a cis- or trans-geometrical isomerism with respect to the double bond; are disclosed.

19 Claims, No Drawings

OTHER PUBLICATIONS

Yabuuchi, T., "Thiophene Derivatives. V. Syntheses of 3-Arylpropionamides" Chemical & Pharmaceutical Bulletin, vol. 8, pp. 169-172, (1960).

Arnall, F., "The Determination of the Relative Strengths of some Nitrogen Bases of the Aromatic Series and of some Alkaloids", Journal of the Chemical Society, vol. 117, pp. 835-839, (1920).

Svein Dueland, et al., "Cholesterol 7α-hydroxylase influences the expression of hepatic apoA-I in two inbred mouse strains displaying different susceptibilities to atherosclerosis and in hepatoma cells", Journal of Lipid Research, vol. 38, pp. 1445-1453, 1997.

Edward M. Rubin et al., "Inhibition of early atherogenesis in transgenic mice by human apolipoprotein AI", Letters to Nature, vol. 353, pp. 265-267, 1991.

Andrew S. Plump et al., "Human apolipoprotein A-I gene expression increases high density lipoprotein and suppresses atherosclerosis in the apolipoprotein E-deficient mouse", Proc. Natl. Acad. Sci., vol. 91, pp. 9607-9611, 1994.

Jean-Michel Robert et al., "Synthesis and Anti-inflammatory Activity of Polyazaheterocyclic Derivatives of 6-Amino-2,4-lutidine and Their Precursors", Arzneim.-Forsch./Drug Res., vol. 47(I), pp. 635-642, 1997.

Akira Miyazaki et al., "Intravenous Injection of Rabbit Apolipoprotein A-I Inhibits the Progression of Atherosclerosis in Cholesterol-Fed Rabbits", Arterioscler. Thromb. Vasc. Biol., vol. 15, pp. 1882-1888, 1995.

Kiyoto Goto et al., "Synthesis and Biological Activity of the Metabolites of Diethyl 4-[(4-Bromo-2-Cyanophenyl) carbamoyl]benzylphosphonate (NO-1886)", Chem. Pharm. Bull., vol. 44(3), pp. 547-551, 1996.

William J. Mergens et al., "In Vitro Nitrosation of Methapyrilene", Journal of Pharmaceutical Sciences, vol. 68, No. 7, pp. 827-832, 1979.

J. M. Robert et al., "Synthesis and Anti-inflammatory Activity of Polyazaheterrocyclic Derivatives of 6-Amino-2,4-lutidine and Their Precursors", Arzneim.-Forsch./Drug Res., 47 (I), pp. 635-642, 1997.

Khromov-Borisov et al. Zhurnal Obshchei Khimii, 27, pp. 695-698. (1957).

John M. Domagala, "Functionalization of Substituted 2(1H)- and 4(1H)-Pyridones. 4. Synthesis of Substituted 6-(Aminocarbonyl)-1,2-dihydro-2-oxo- and 6-(Aminocarbonyl)-1,4,-dihydro-4-oxo-3-p3rridinecarboxylic Acids", Journal of Organic Chemistry, 49(1), pp. 126-130. (1984).

K. Takatori et al., "Syntheses of the Amides Derived from Heterocyclic Acids and Heterocyclic Amines and their Antitumor Activities" (with abstract), Journal of the Pharmaceutical Society of Japan, 96(4), pp. 471-474. (1976).

S. Biniecki et al., "Synthesis of Methyl-2-Pyridylamides of Pyridine-3-Carboxylic Acid" (with summary), Acta Poloniae Pharmaceutica, 32(3), pp. 269-272. (1975).

R. Herbert et al., "Syntheses and Properties of 1*H*-Pyrrolo[2,3-*b*]pyridines" Journal of the Chemical Society [Section] C: Organic, (II), pp. 1505-1514. (1969).

J.M.H. Robert et al. "Non-carboxylic antiinflammatory compounds. III. *N*-(4,6-Dimethylpyridin-2-yl)arylcarboxamides and arylthfocarboxamides acting as brain edema inhibitors", European Journal of Medicinal Chemistry, 30(12), pp. 915-924. (1995).

S. Biniecki et al., "Syntheses of 3-, 4-, 5- and 6-Methyl-2-Pyridylamides of Furane-2-Carboxylic Acid" (with summary), Acta Poloniae Pharmaceutica, 34(4), pp. 341-343. (1977).

A.L. Mnjoian, et al. "The Effect of Organic Acids Pyridyl and Thiazolylamides on certain members of *Coli-typhosal, Staphylococcal, Streptococcal* Groups and that of Acid Resistant Mycobacteria" (with summary), Biolgicheski Svoistva Khimicheskikh Soedinenii, pp. 219-233. (1962).

G.A. White "Furan Carboxamide Fungicides: Structure-Activity Relationships with the Succinate Dehydrogenase Complex in Mitochondria from a Wild-Type Strain and a Carboxin-Resistant Mutant Strain of *Ustilago maydis*", Pesticide Biochemisty and Physiology, 31(2), pp. 129-145. (1988).

\* cited by examiner

# UTILITIES OF AMIDE COMPOUNDS

This application is a divisional application of Ser. No. 10/489,333 filed Apr. 21, 2004 now U.S. Pat. No. 7,429,593, which is a 371 application of PCT/JP01/07980 filed Sep. 14, 2001.

FIELD OF THE INVENTION

This invention relates to a method for enhancing the expression of apolipoprotein AI, and novel compounds therefor.

BACKGROUND ART

Cholesterol is well known as a main etiologic factor for arteriosclerosis that causes severe heart diseases. Especially, increased levels of serum low density lipoprotein (LDL) are believed to be a definite risk factor for coronary heart diseases (CHDs). Remedies for decreasing the level of LDL-cholesterol (LDL-C) in plasma by use of statins have been shown to be clinically effective in preventing the onset of CHDs and improving the conditions of CHDs and survivals in patients suffering from hypercholesterolemia. However, about 40% of CHDs patients have a normal level of LDL-C, and are not always cured effectively by remedies for decreasing the level of LDL-C. On the other hand, it has been known that a half of CHDs patients having a normal level of LDL-C shows a lower level of high density lipoprotein (HDL) cholesterol (HDL-C).

Recently, the lower level of serum HDL-C has been shown to be an additional risk factor of the onset and the recurrence of CHD.

HDL plays an important role in reverse cholesterol transport system that is known as a biological mechanism to transfer an excess cholesterol in cells back to liver so as to maintain the level of cholesterol in living bodies normally.

Lipoproteins such as HDL is mainly comprised of lipids and proteins called apoprotein, and HDL comprises an apoprotein as referred to apolipoprotein AI (hereinafter, made up by apoAI) as a main component.

Excess free cholesterols (FCs) and phospholipids in peripheral cells are extracted by free apoAI to form lipoproteins called preβ-HDL(s). The excess FCs integrated in the preβ-HDLs are transformed into cholesteryl esters (CEs) by lecithin:cholesterol acyl transferase (LCAT), while the preβ-HDLs increase in their particle size to mature into spherical HDLs (HDL3s). The matured HDLs are classified into diverse subfractions based on the density, and these particles further grow up to form HDL2(s). CEs are continuously transferred into very low density lipoprotein (VLDL) and LDL by means of cholesterol ester-transporter protein (CETP). Those lipoproteins that integrate CEs are finally taken into the liver via receptors. During the course, apoAI is regenerated, and again interacts with peripheral cells to repeat the extraction of cholesterols and the regeneration of preβ-HDLs.

It has been well understood that HDL plays a central role in reverse cholesterol transport system and is a defensive factor of arteriosclerosis. It is expected that agents that promote the HDL functions could be clinically effective as medicaments for treating arteriosclerotic diseases. Accordingly, studies to develop agents that enhance the level of HDL in plasma have been conducted via various approaches.

Among them, one of the most promising approaches is to enhance the serum level of apoAI, a main component of HDL. It is understood that apoAI production increased by enhancing the expression of apoAI gene leads to directly the elevation of HDL-C level in plasma, resulting in the activation of reverse cholesterol transport system. In fact, it has been demonstrated that the mRNA level of apoAI in liver correlates closely with the levels of apoAI and HDL-C in blood (Dueland S., France D., Wang S L., Trawick J D., and Davis R A., J. Lipid Res., 38:1445-53 (1997), "Cholesterol 7alpha-hydroxylase influences the expression of hepatic apoA-I in two inbred mouse strains displaying different susceptibilities to atherosclerosis and in hepatoma cells."). In addition, it has been shown that apoAI-transgenic mice and rabbit pathologic models administered with apoAI exhibit anti-arteriosclerosis activities (Rubin E. M., Krauss R. M., Spangler E. A., Verstuyft J. G., and Clift S. M., Nature 353, 265-267 (1991), "Inhibition of early atherogenesis in transgenic mice by human apolipoprotein AI."; Plump A. S., Scott C. J., Breslow J. L., Proc. Natl. Acad. Sci. USA., 91, 9607-9611 (1994), "Human apolipoprotein A-I gene expression increases high density lipoprotein and suppress atherosclerosis in the apolipoprotein E-deficient mouse."; Miyazaki A., Sakuma S., Morikawa W., Takiue T., Miake F., Terano T., Sakai M., Hakamata H., Sakamoto Y., et al., Arterioscler. Thromb. Vasc. Biol., 15, 1882-1888 (1995), "Intravenous injection of rabbit apolipoprotein A-I inhibits the progression of atherosclerosis in cholesterol-fed rabbits.").

All those facts clearly suggest that agents that enhance the expression of apoAI would be candidates for medicaments of dyslipidemia, arteriosclerotic diseases, and other diverse diseases associated with HDL.

Compounds similar to the compounds according to the invention in terms of chemical structure are described in GB2327675, WO99/07669, WO99/24404, U.S. Pat. No. 5,670,066, DE19734438, Japanese Patent Publication (kokai) No. 41118/1994, Japanese Patent Publication (kokai) No. 14568/1991, Japanese Patent Publication (kokai) No. 253974/1992, Japanese Patent Publication (kokai) No. 147874/1999, and Journal of Pharmaceutical Sciences vol. 68, No. 7, 827-832, but the activities of these compounds are quite different from the activities according to the present invention.

Several compounds that have a chemical structure similar to the compounds of the invention, and that are described to be effective in treatment of hyperlipidemia, arteriosclerosis, and visceral fat syndrome have been known. Japanese Patent Publication (kokai) No. 68592/1991 describes the compounds that lower the level of triglycerides in plasma and consequently enhance the level of HDL-C, but the effect is caused by activating lipoprotein lipases (Goto, K., Nakamura, S., Morioka, Y., Kondo, M., Naito, S., Tsutsumi, K., Chem. Pharm. Bull., 44, 547-551 (1996), "Synthesis and Biological Activity of the Metabolites of Diethyl 4-[(4-Bromo-2-cyanophenyl)carbamoyl]-benzylphosphonate (NO-1886)"). WO98/39280 and WO98/02412 describe the compounds that inhibit acyl-CoA cholesterol acyltransferase (ACAT) thereby suppressing the accumulation of cholesterol in macrophage. Japanese Patent Publication (kokai) No. 171848/1999 describes the compounds that inhibit acetyl-CoA carboxylase thereby suppressing the biosynthesis of triglycerides. WO99/07382 describes the compounds that have an antagonist activity of macrophage scavenger receptors. Japanese Patent Publication (kokai) No. 158133/1999 describes the compounds that have activities for suppressing LDL oxidation and inhibiting ACAT. As described above, the known compounds are quite different from the compounds of the invention in terms of action mechanism.

Compounds that increase apoAI are described in Japanese Patent Publication (kokai) No. 221959/1993, Japanese Patent Publication (kokai) No. 291094/1996, and WO97/09048, but those compounds are different from the compounds of the invention in chemical structure.

DISCLOSURE OF THE INVENTION

The present invention is directed to methods for enhancing the expression of apoAI, and novel compounds having the activity thereof.

Specifically, the invention provides

1) A method of enhancing the expression of apoAI, which comprises administrating a therapeutically effective amount of a compound of formula (I):

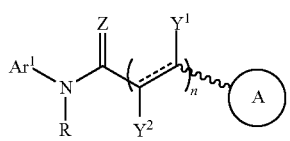

(I)

in which
ring A is $Ar^2$ or a group of

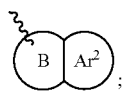

$Ar^1$ and $Ar^2$ are independently a monocyclic or bicyclic aromatic carbocyclic group that may be optionally substituted, or a monocyclic or bicyclic aromatic heterocyclic group that may be optionally substituted;

ring B is a monocyclic non-aromatic carbocyclic group that may be optionally substituted, or a monocyclic non-aromatic heterocyclic group that may be optionally substituted;

R is a hydrogen or a lower alkyl that may be optionally substituted;

Z is oxygen or sulfur;

$Y^1$ and $Y^2$ are independently a hydrogen, a halogen, a lower alkyl that may be optionally substituted, a carboxy, a lower alkoxycarbonyl that may be optionally substituted, a cyano, a phenyl that may be optionally substituted, or a monocyclic aromatic heterocyclic group that may be optionally substituted, and two $Y^1$s or more and two $Y^2$s or more each may be different among them;

n is an integer of 0 to 2;

the broken line is independently the presence or absence of a bond; and the wavy line represents a cis- or trans-geometrical isomerism with respect to the double bond; a prodrug thereof, a pharmaceutically acceptable salt or solvate of them to a patient expected to enhance the expression of apoAI;

2) The method according to above 1), in which $Ar^1$ in formula (I) is a monocyclic or bicyclic aromatic heterocyclic group that may be optionally substituted, and that contains a nitrogen atom at the position adjacent to the constituent atom of the ring that has a binding bond;

3) The method according to above 1), in which $Ar^1$ in formula (I) is 2-pyridyl, 2-quinolyl, 2-quinoxalyl, 2-benzisoxazolyl, 2-benzothiazolyl, or 2-benzimidazolyl, each of which may be optionally substituted;

4) The method according to any one of above 1) to 3), in which $Ar^2$ in formula (I), which is condensed with ring B, is a benzene ring that may be optionally substituted, or a monocyclic aromatic heterocyclic group that may be optionally substituted;

5) The method according to any one of above 1) to 3), in which ring A in formula (I) is a phenyl that may be optionally substituted, or a monocyclic aromatic heterocyclic group that may be optionally substituted;

6) The method according to above 5), in which ring A in formula (I) is a phenyl or a monocyclic aromatic heterocyclic group, each of which may be optionally substituted, wherein the substituent is a halogen; a lower alkyl optionally substituted by a halogen or a lower alkoxy; a hydroxy; a lower alkoxy; phenoxy; naphthyloxy; an acyloxy; a carboxy; a lower alkoxycarbonyl; an amino optionally substituted by a lower alkyl or a lower acyl; a phenyl that may be optionally substituted by a lower alkoxy; a nitro; a lower alkylthio; a cyano; a monocyclic heterocyclic group; or an alkylenedioxy;

7) The method according to any one of above 1) to 6), in which $Y^1$ and/or $Y^2$ in formula (I) is a hydrogen;

8) The method according to any one of above 1) to 7), in which Z in formula (I) is oxygen;

9) The method according to any one of above 1) to 8), in which n in formula (I) is 1 or 2, and all of the broken line are the presence of a bond;

10) The method according to above 9), in which when n is 1 and the broken line is the presence of a bond, then the wavy line represents trans configuration with respect to the relationship between NRCZ and ring A, or alternatively when n is 2 and the broken lines are the presence of a bond, then the wavy line represents trans configuration with respect to the relationship between NRCZ and $CY^2$ and/or the relationship between $CY^1$ and ring A;

11) A method of treatment or prevention of dyslipidemia or arteriosclerotic diseases, which comprises administrating a therapeutically effective amount of a compound of formula (I) as defined in above 1), a prodrug thereof, a pharmaceutically acceptable salt or solvate of them to a patient suspected to have dyslipidemia or arteriosclerotic diseases; preferably the method thereof which comprises administrating a therapeutically effective amount of the compound as defined in any one of above 2) to 10), a prodrug thereof, a pharmaceutically acceptable salt or solvate of them;

12) A compound of formula (II):

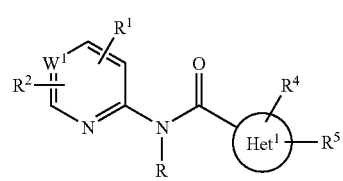

(II)

in which
$Het^1$ is pyridyl, furyl, 3-thienyl or pyrrolyl;
R is a hydrogen, or a lower alkyl;
$W^1$ is $CR^3$ or N; and
$R^1$, $R^2$, $R^3$, $R^4$ and $R^5$ are independently a hydrogen, a hydroxy, a lower alkyl, a lower alkoxy, a carboxy, a lower alkoxycarbonyl, an amino, a lower alkylamino, or an acyl; a prodrug thereof, a pharmaceutically acceptable salt or solvate of them;

13) A compound of formula (III):

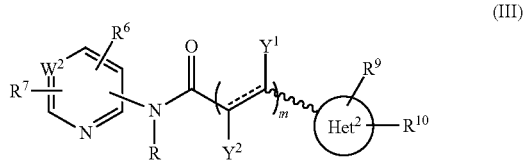

in which
Het² is pyridyl, furyl, thienyl or pyrrolyl;
R is a hydrogen, or a lower alkyl that may be optionally substituted;
W² is CR⁸ or N;
Y¹ and Y² are independently a hydrogen, a halogen, a lower alkyl that may be optionally substituted, a carboxy, a lower alkoxycarbonyl that may be optionally substituted, a cyano, a phenyl that may be optionally substituted, or a monocyclic aromatic heterocyclic group that may be optionally substituted;
R⁶, R⁷, R⁸, R⁹ and R¹⁰ are independently a hydrogen, a halogen, a hydroxy, a lower alkyl that may be optionally substituted, a lower alkoxy that may be optionally substituted, a carboxy, a lower alkoxycarbonyl that may be optionally substituted, an amino that may be optionally substituted, or an acyl that may be optionally substituted;
any two of R⁶, R⁷, and R⁸ may be combined to form a cyclic ring group;
m is 1 or 2;
the broken line is independently the presence or absence of a bond; and
the wavy line represents a cis- or trans-geometrical isomerism with respect to the double bond; a prodrug thereof, a pharmaceutically acceptable salt or solvate of them;
14) The compound according to above 13), in which W² is CH; R is a hydrogen or a lower alkyl, and all of the broken line are the presence of a bond; a prodrug thereof, a pharmaceutically acceptable salt or solvate of them;
15) A pharmaceutical composition, which comprises the compound according to any one of above 12) to 14), a prodrug thereof, a pharmaceutically acceptable salt or solvate of them, together with a pharmaceutically acceptable additive;
16) The pharmaceutical composition according to above 15), which is used to enhance the expression of apoAI; and
17) The pharmaceutical composition according to above 15), which is used for prevention and/or treatment of dyslipidemia or arteriosclerotic diseases.

Further, the invention provides a method of enhancing the expression of apoAI, and a method of prevention or treatment of dyslipidemia or arteriosclerotic diseases, both of which comprises administrating a therapeutically effective amount of a compound of formula (II) or (III) as described above: a prodrug thereof, a pharmaceutically acceptable salt or solvate of them.

As used herein, each two Y¹s and Y²s as resulted from the case that n is 2 may be different each other.

The term "halogen" as used herein includes fluorine, chlorine, bromine and iodine.

The term "lower alkyl" as used herein refers to a straight or branched chain alkyl comprising 1 to 6 carbon atoms, preferably 1 to 3 carbon atoms. Examples of the lower alkyl include methyl, ethyl, n-propyl, isopropyl, n-butyl, isobutyl, sec-butyl, tert-butyl, n-pentyl, isopentyl, neopentyl, hexyl, isohexyl, and the like.

The term "lower alkyl that may be optionally substituted" as used herein includes a lower alkyl, of which any position may be substituted by one or more substituents. The substituent includes a halogen, a hydroxy, a lower alkoxy, a monocyclic or bicyclic carbocyclic group, an acyl, an acyloxy, a carboxy, a lower alkoxycarbonyl, an amino, a lower alkylamino, a nitro, a monocyclic or bicyclic heterocyclic group, and the like.

Alkyl moiety of "lower alkoxy", "lower alkylthio" or "lower alkylamino" is similar to the "lower alkyl" as described above.

The term "alkylenedioxy" specifically includes methylenedioxy, ethylenedioxy, and the like.

Substituent in "lower alkoxy that may be optionally substituted" is similar to the substituent of "lower alkyl that may be optionally substituted" as described above.

Lower alkyl moiety of "lower alkoxycarbonyl" is similar to the "lower alkyl" as described above, and substituent of "lower alkoxycarbonyl that may be optionally substituted" is similar to the substituent of "lower alkyl that may be optionally substituted" as described above.

The term "acyl" includes an aroyl and an aliphatic acyl containing 1 to 7 carbon atoms. Here, "aroyl" refers to a group wherein a carbonyl group is bonded to an aromatic carbocyclic group or an aromatic heterocyclic group. Examples of the acyl include formyl, acetyl, propionyl, butyryl, isobutyryl, valery, pivaloyl, hexanoyl, acryloyl, propioloyl, methacryloyl, crotonoyl, and benzoyl. Acyl moiety of "acyloxy" is similar to the "acyl".

Substituent of "acyl that may be optionally substituted" is similar to the substituent of the "lower alkyl that may be optionally substituted" as described above, and the aroyl may be substituted by a lower alkyl. Acyl may be substituted at one or more arbitrary positions by such a substituent.

The term "amino that may be optionally substituted" includes an unsubstituted, mono-substituted, or di-substituted amino. Examples of the substituents include the substituents of the "lower alkyl that may be optionally substituted" as described above.

The term "monocyclic non-aromatic carbocyclic group" as used herein refers to a cyclic ring group containing 3 to 10 carbon atoms, preferably 5 to 8 carbon atoms, and includes a non-aromatic cyclic group that may contain one or more double bond at any position. Examples includes cyclopropyl, cyclobutyl, cyclopentyl, cyclopentenyl, cyclohexyl, cyclohexenyl, cycloheptyl, cycloheptenyl, cycloheptadienyl, cyclooctyl, cyclooctenyl, cyclooctadienyl, cyclononyl, and cyclodecyl.

The term "monocyclic carbocyclic group" as used herein refers to a cyclic ring group containing 3 to 10 carbon atoms, preferably 5 to 8 carbon atoms, and includes "monocyclic non-aromatic carbocyclic group" as described above, and a phenyl.

The term "monocyclic aromatic carbocyclic group" as used herein refers to a phenyl (or a benzene ring).

The term "monocyclic aromatic heterocyclic group" refers to an aromatic heterocyclic group containing one or more hetero atoms selected from the group consisting of N, S and O within its ring. Examples include pyrrolyl, imidazolyl, pyrazolyl, pyridyl, pyridazinyl, pyrimidyl, pyrazinyl, triazolyl, triazinyl, tetrazolyl, isoxazolyl, oxazolyl, oxadiazolyl, isothiazolyl, thiazolyl, thiadiazolyl, furyl, and thienyl.

The term "monocyclic non-aromatic heterocyclic group" refers to a non-aromatic cyclic group wherein one or more carbon atoms that are contained in the "monocyclic non-aromatic carbocyclic group" as described above, and that can be substituted, are substituted by a hetero atom selected from the group consisting of N, S and O. Examples include dioxanyl, dioxazinyl, dioxolanyl, dioxolyl, dithiazinyl, imidazolidinyl, imidazolinyl, morpholyl, oxazinyl, oxadiazyl, furazaryl, oxathianyl, oxathiazinyl, oxathiolanyl, oxazolinyl, oxazolinyl, piperazinyl, piperidinyl, pyranyl, pyrazolidinyl, pyrazolinyl, pyrrolidinyl, pyrrolinyl, tetrahydropyranyl, thiadiazolidinyl, thianyl, thiazinyl, thiadiazinyl, thiiranyl, and thiolanyl.

The term "monocyclic heterocyclic group" includes "monocyclic aromatic heterocyclic group" and "monocyclic non-aromatic heterocyclic group" as described above, and include preferably pyridyl, pyrimidinyl, pyrrolyl, furyl, thienyl, and thiazolyl.

Heterocyclic moiety of "monocyclic aromatic heterocyclic oxy" is similar to the aromatic heterocyclic group as described above.

The term "bicyclic carbocyclic group" refers to an aromatic or non-aromatic cyclic group containing 6 to 12 carbon atoms wherein two cyclic rings are condensed. Examples include naphthyl, indanyl, indenyl, dihydronaphthyl, and tetrahydronaphthyl, and preferably, naphthyl.

The term "bicyclic aromatic carbocyclic group" refers to naphthyl (or a naphthalene ring).

The term "bicyclic heterocyclic group" includes a cyclic ring compound wherein one or more carbon atoms that are contained in the "bicyclic carbocyclic group" as described above, and that can be substituted, are substituted by a hetero atom selected from the group consisting of N, S and O. Examples include aromatic heterocyclic groups such as indolyl, isoindolyl, indolizinyl, benzimidazolyl, indazolyl, cinnolinyl, phthalazinyl, benzoxazolyl, benzisoxazolyl, benzoxadiazolyl, benzothiazolyl, benzisothiazolyl, benzothiadiazolyl, benzofuryl, isobenzofuryl, benzothienyl, benzotriazolyl, imidazopyridyl, triazolopyridyl, imidazothiazolyl, pyrazinopyridazinyl, quinazolinyl, quinolyl, isoquinolyl, quinoxalinyl, purinyl, pteridinyl, naphthylidinyl, and pyrazinopyridazinyl, and non-aromatic heterocyclic groups such as chromanyl, 2H-chromenyl, coumarinyl, coumaranonyl, 1,3-dioxaindanyl, indolinyl, isoindolinyl, dihydroquinolyl, dihydroisoquinolyl, tetrahydroquinolyl, tetrahydroisoquinolyl, 6,7-dihydro-5H-[1]pyrimidinyl, benzothiazinyl, tetrahydroquinoxalyl, cyclopentenopyridinyl, 4,5,6,7-tetrahydro-1H-indolyl, 4-oxochromenyl, 3,4-dihydro-2H-benzo[1,4]oxazinyl, and pyrrolidinyl. Preferable examples include indolyl, benzimidazolyl, benzoxazolyl, benzoxadiazolyl, benzothiazolyl, benzothiadiazolyl, benzofuryl, benzothienyl, imidazopyridyl, triazolopyridyl, quinolyl, isoquinolyl, and quinoxalinyl.

The term "bicyclic aromatic heterocyclic group" refers to only an aromatic heterocyclic group among the groups of "bicyclic heterocyclic group" as described above.

Substituent in "monocyclic or bicyclic carbocyclic group that may be optionally substituted", "monocyclic carbocyclic group that may be optionally substituted", "phenyl that may be optionally substituted", and "monocyclic or bicyclic aromatic carbocyclic group that may be optionally substituted" includes a halogen; a hydroxy; a lower alkyl optionally substituted by a halogen, a hydroxy, or a lower alkoxy; a lower alkoxy optionally substituted by a halogen, a hydroxy, a carboxy, or a lower alkoxycarbonyl; a lower alkenyl optionally substituted by a halogen, a hydroxy, a carboxy, or a lower alkoxycarbonyl; a lower alkenyloxy optionally substituted by a halogen or a hydroxy; a lower alkylthio; a non-aromatic carbocyclic group optionally substituted by a halogen, a hydroxy, or a lower alkyl; an acyl; an acyloxy; a carboxy; a lower alkoxycarbonyl; a lower alkenyloxycarbonyl; an amino optionally substituted by a lower alkyl or an acyl; a hydrazino, a nitro; a cyano; a monocyclic or bicyclic aromatic carbocyclic group optionally substituted by a halogen, a hydroxy, a lower alkyl, or a lower alkoxy; a monocyclic or bicyclic heterocyclic group; a phenoxy optionally substituted by a halogen, a hydroxy, or a lower alkyl; a monocyclic aromatic heterocyclic oxy; an oxo; and an alkylenedioxy, all of which may be bonded at one or more arbitrary positions.

Preferable examples include a halogen; a hydroxy; a lower alkyl optionally substituted by a halogen or a hydroxy; a lower alkoxy optionally substituted by a halogen, a hydroxy, a carboxy, or a lower alkoxycarbonyl; a lower alkenyl optionally substituted by a halogen, a hydroxy, a carboxy, or a lower alkoxycarbonyl; a lower alkylthio; an acyl; an acyloxy; a carboxy; a lower alkoxycarbonyl; an amino optionally substituted by a lower alkyl or an acyl; a hydrazino, a nitro; a cyano; a phenyl; a monocyclic or bicyclic heterocyclic group; an oxo; and an alkylenedioxy.

Substituent in "monocyclic aromatic heterocyclic group that may be optionally substituted", "monocyclic non-aromatic heterocyclic group that may be optionally substituted", "monocyclic heterocyclic group that may be optionally substituted", "monocyclic aromatic heterocyclic group that may be optionally substituted", "monocyclic or bicyclic aromatic heterocyclic group that may be optionally substituted", "2-pyridyl that may be optionally substituted", and "2-pyridyl, 2-quinolyl, 2-quinoxalyl, 2-benzisoxazolyl, 2-benzothiazolyl, or 2-benzimidazolyl, each of which may be optionally substituted" is similar to the substituent in "monocyclic or bicyclic carbocyclic group that may be optionally substituted" and the like as described above. Preferable examples include a halogen; a hydroxy; a lower alkyl optionally substituted by a lower alkoxy; a lower alkoxy; a lower alkenyl; a lower alkylthio; an acyl; an acyloxy; a carboxy; a lower alkoxycarbonyl; an amino optionally substituted by a lower alkyl; and a phenyl and a monocyclic heterocyclic group optionally substituted by a lower alkoxy.

The term "a monocyclic or bicyclic aromatic heterocyclic group that contains a nitrogen atom at the position adjacent to the constituent atom of the ring that has a binding bond" includes "a monocyclic or bicyclic aromatic heterocyclic group" as described above that has a binding bond to NRCZ at ortho position with respect to the N atom that constitutes a ring. Specific examples include monocyclic aromatic heterocyclic groups such as 2-pyridyl, 2- or 4-pyrimidinyl, 3-pyridazinyl, 2-pyrazinyl, 1,3,5-triazin-2-yl, 2-pyrrolyl, 1- or 3-pyrazolyl, 2- or 4-imidazolyl, 2- or 4-oxazolyl, 3-isoxazolyl, 1,3,4-oxadiazol-2-yl, 1,3-thiazol-2-yl, 1,3-thiazol-4-yl, 1,2,5-thiadiazol-3-yl, 1,2,3-thiadiazol-4-yl, 1,3,4-thiadiazol-2-yl, 3-isothiazolyl, 1,2,3-triazol-4-yl, 1H-tetrazol-1-yl, and 1H-tetrazol-5-yl; and bicyclic aromatic heterocyclic groups such as 2-benzimidazolyl, 3-benzisothiazolyl, 3-benzisoxazolyl, 2-benzoxazolyl, 2-benzothiazolyl, 1-benzotriazolyl, 1- or 3-indazolyl, 3-cinnolinyl, 2-indolyl, 1- or 3-isoindolyl, 2-naphthylidinyl, 2-, 4-, 6- or 7-pteridinyl, 2-, 6 or 8-purinyl, 1- or 3-isoquinolyl, 2-quinolyl, 2- or 4-quinazolinyl, and 2-quinoxalinyl. Those substituents may be bonded at one or more arbitrary positions similarly to "monocyclic or bicyclic carbocyclic group that may be optionally substituted" as described above.

The phrase "any two of $R^6$, $R^7$, and $R^8$ are combined to form a cyclic ring group" means that any two of $R^6$, $R^7$, and $R^8$ are combined with a constituent atom of a pyridine or pyrimidine ring to which they are bonded to form a non-aromatic carbocyclic group, a benzene ring, or a heterocyclic group. Specific examples include quinolyl, isoquinolyl, quinazolinyl, pteridinyl, purinyl, pyridoxazinyl, tetrahydroquinolyl, tetrahydroisoquinolyl, or tetrahydroquinazolinyl.

A group of the formula:

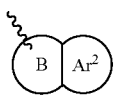

refers to a bicyclic or tricyclic group, preferably a bicyclic group, which is formed by condensing ring B with Ar². Ring B means a 4- to 7-membered non-aromatic carbocyclic group or non-aromatic heterocyclic group, which may contain one or more double bonds at any position. A constituent atom of ring B and Ar² may be carbon, nitrogen, oxygen, or sulfur.

Preferable ring B includes a moiety of the formula:

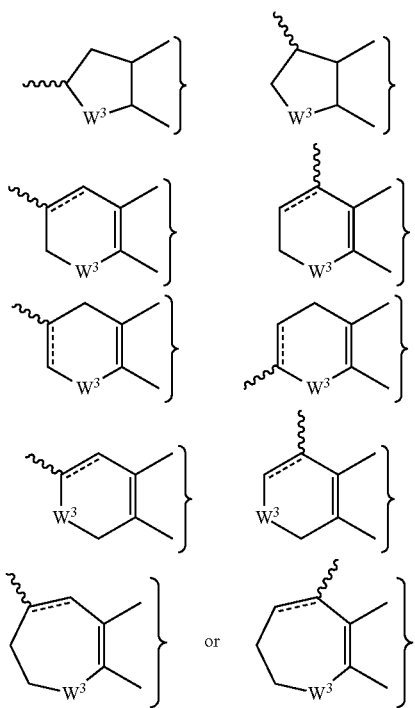

or wherein $W^3$ is $CR^{11}R^{12}$, O, $NR^{13}$, or S;

$R^{11}$, $R^{12}$, and $R^{13}$ are independently a hydrogen, a halogen, a hydroxy; a lower alkyl optionally substituted by a halogen or a hydroxy; a lower alkoxy optionally substituted by a halogen, a hydroxy, a carboxy, or a lower alkoxycarbonyl; a lower alkenyl optionally substituted by a halogen, a hydroxy, a carboxy, or a lower alkoxycarbonyl; a lower alkylthio; an acyl; an acyloxy; a carboxy; a lower alkoxycarbonyl; an amino optionally substituted by a lower alkyl or an acyl; a hydrazino, a nitro; a cyano; a phenyl; or a heterocyclic group; and $R^{11}$ and $R^{12}$ may be combined to form an oxo; and the broken line is the presence or absence of a bond.

Examples of Ar² to be condensed with ring B include a benzene ring. In this case, specific examples of ring A include 1-, 2-, 3- or 4-dihydronaphthalenyl, 1-, 2- or 3-indolinyl, 1- or 2-indanyl, 1-, 2- or 3-indenyl, 1- or 2-tetrahydronaphthalenyl, 2-, 3- or 4-1,2-dihydroquinolinyl, 3- or 4-isochromanyl, 2-, 3- or 4-chromanyl, 2-, 3- or 4-chromenyl, 2-, 3- or 4-thiochromenyl, 2-, 3- or 4-benzothiopyranyl, 2- or 3-dihydrobenzothienyl, 2- or 3-dihydrobenzofuryl, 2-benzo[1,3]dioxolyl, 2-2,3-dihydrobenzo[1,4]dioxonyl, 2- or 3-3,4-dihydro-2H-benzo[1,4]oxadinyl, 8- or 9-6,7-dihydro-5H-benzocycloheptenyl, and 2-, 3- or 4-oxo-4H-chromenyl.

In addition to a benzene ring, example of Ar² to be condensed with ring B include 6-membered cyclic groups such as pyridine, pyrazine, and pyrimidine; 5-membered cyclic groups such as pyrrole, furan, thiophene, oxazole, isoxazole, and thiazole; and bicyclic aromatic cyclic groups such as quinoline, isoquinoline, and indole, all of which may be replaced for a benzene contained in the examples of ring A as described above.

Ring B and Ar² may be substituted by a substituent at any position which is similar to those of a monocyclic or bicyclic carbocyclic group that may be optionally substituted.

The compounds according to the invention include pharmaceutically acceptable, producible salts. Examples of the "pharmaceutically acceptable salts" include a salt with an inorganic acid e.g. those with hydrochloric acid, sulfuric acid, nitric acid, phosphoric acid, or the like; a salt with an organic acid e.g. those with p-toluenesulfonic acid, methanesulfonic acid, oxalic acid, citric acid, or the like; a salt with an organic base e.g. ammonium, trimethylammonium, triethylammonium, or the like; a salt with an alkaline metal e.g. sodium, potassium, or the like; a quaternary salt with alkyl halide e.g., methyl iodide, ethyl iodide or the like; and a salt with an alkaline earth metal e.g., calcium, magnesium, or the like.

The compounds according to the invention may form solvates as coordinated with a suitable organic solvent and/or water. Hydrates are exemplified.

The compounds according to the invention also include prodrugs. In the context of the invention, a "prodrug" is a derivative of a compound according to the invention comprising a chemically or metabolically cleavable group. In the course of metabolism in the body, a prodrug shows a pharmacological activity as a result of conversion to the compounds according to the invention. Method for selecting and producing suitable prodrug derivatives are described in, e.g. "Design of Prodrugs, Elsevier, Amsterdam (1985)".

Prodrugs of a compound according to the invention having a carboxy are exemplified by an ester derivative prepared by condensing the carboxy group with a suitable alcohol, and alternatively by an amide derivative prepared by reacting the carboxy and a suitable amine.

Prodrugs of a compound according to the invention having a hydroxy are exemplified by an acyloxy derivative prepared by reacting the hydroxy group and a suitable acyl halide or a suitable acid anhydride.

Prodrugs of a compound according to the invention having an amino are exemplified by an amide derivative prepared by reacting the amino group and a suitable acid halide or a suitable mixed anhydride compound.

When compound (I) according to the invention has asymmetric carbon atom(s), then the invention encompasses a racemate, both of enantiomers, and all of diastereomers. When compound (I) according to the invention has a double bond, the invention includes both of geometric isomers resulting from possible arrangements of its substituents.

Although all of the compounds according to the invention have an activity for enhancing the expression of apoAI, the following compounds can be listed as preferable compounds. In formula (I):

1) a compound wherein Ar¹ is a monocyclic or bicyclic aromatic carbocyclic group that may be optionally substituted, or a monocyclic or bicyclic aromatic heterocyclic group that may be optionally substituted wherein the substituent is a halogen; a lower alkyl optionally substituted by a halogen; a hydroxy; a lower alkoxy; an aryloxy; an acyloxy; a carboxy; a lower alkoxycarbonyl; an amino optionally substituted by a lower alkyl or a lower acyl; a phenyl; a nitro; a lower alkylthio; a cyano; a monocyclic heterocyclic group; or an alkylenedioxy (hereinafter, Ar¹ is regarded as Ar1-a);

a compound wherein Ar¹ is a monocyclic or bicyclic aromatic heterocyclic group that may be optionally substituted, and that contains a nitrogen atom at the position adjacent to the constituent atom of the ring that has a binding bond wherein the substituent is similar to those in Ar1-a (hereinafter, Ar¹ is regarded as Ar1-b);

a compound wherein Ar¹ is a monocyclic or bicyclic aromatic heterocyclic group that may be optionally substituted by a lower alkyl or an amino, and that contains a nitrogen atom at the position adjacent to the constituent atom of the ring that has a binding bond (hereinafter, Ar¹ is regarded as Ar1-c);

a compound wherein Ar¹ is an unsubstituted monocyclic or bicyclic aromatic heterocyclic group, and that contains a nitrogen atom at the position adjacent to the constituent atom of the ring that has a binding bond (hereinafter, Ar¹ is regarded as Ar1-d);

a compound wherein Ar¹ is 2-quinolyl, 2-quinoxalyl, 2-benzimidazolyl, 2-thiazolyl, 2-benzothiazolyl, 2-oxazolyl, 2-benzoxazolyl, 2-oxadiazolyl, 2-pyridyl, 2-pyrimidyl, or 2-imidazolyl (hereinafter, Ar¹ is regarded as Ar1-e);

2) a compound wherein ring A is a monocyclic or bicyclic aromatic carbocyclic group that may be optionally substituted, or a monocyclic or bicyclic aromatic heterocyclic group that may be optionally substituted wherein the substituent is a halogen; a lower alkyl optionally substituted by a halogen; a hydroxy; a lower alkoxy; an aryloxy; an acyloxy, a carboxy; a lower alkoxycarbonyl; an amino optionally substituted by a lower alkyl or a lower acyl; a phenyl; a nitro; a lower alkylthio; a cyano; a monocyclic heterocyclic group; or an alkylenedioxy (hereinafter, ring A is regarded as A-a);

a compound wherein ring A is a monocyclic or bicyclic aromatic carbocyclic group that may be optionally substituted, or a monocyclic or bicyclic aromatic heterocyclic group that may be optionally substituted wherein the substituent is a halogen; a lower alkyl optionally substituted by a halogen; an acyloxy; a lower alkoxy; an alkylenedioxy; or a phenyl (hereinafter, ring A is regarded as A-b);

a compound wherein ring A is a monocyclic or bicyclic aromatic heterocyclic group that is not substituted (hereinafter, ring A is regarded as A-c);

a compound wherein ring A is a phenyl, 2-naphthyl, 2- or 3-furyl, 2- or 3-thienyl, 2- or 3-pyrrolyl, 2-, 3- or 4-pyridyl, 2-indolyl, 2-benzofuryl, 6-quinolyl, 2- or 6-benzothienyl, or 3-2H-chromenyl (hereinafter, ring A is regarded as A-d);

a compound wherein ring A is a group of the formula:

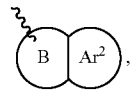

and Ar² is A-a (hereinafter, ring A is regarded as A-e);

a compound wherein ring A is a group of the formula:

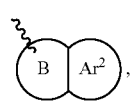

and Ar² is A-b (hereinafter, ring A is regarded as A-f);

a compound wherein ring A is a group of the formula:

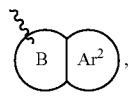

and Ar² is A-c (hereinafter, ring A is regarded as A-g);

a compound wherein ring A is a group of the formula:

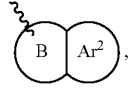

and Ar² is benzene, pyridine, pyrazine, pyrimidine, pyrrole, furan, thiophene, oxazole, isoxazole, thiazole, quinoline, isoquinoline, or indole, and ring B is a moiety of the formula:

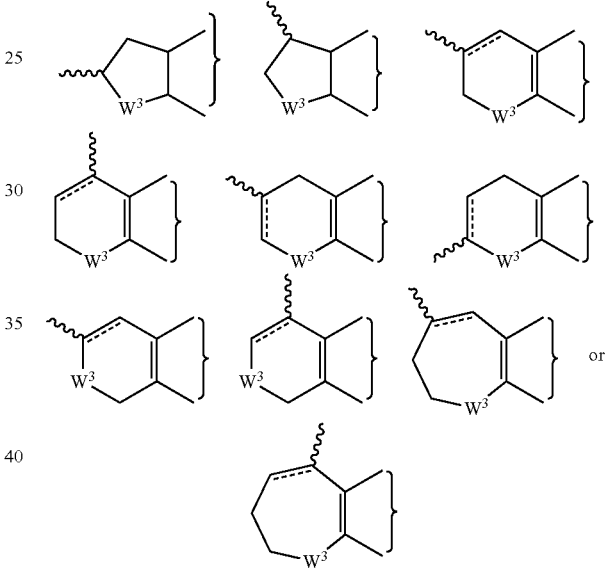

or wherein $W^3$ is $CR^{11}R^{12}$, O, $NR^{13}$, or S;

$R^{11}$, $R^{12}$, and $R^{13}$ are independently a hydrogen, a halogen, a hydroxy; a lower alkyl optionally substituted by a halogen or a hydroxy; a lower alkoxy optionally substituted by a halogen, a hydroxy, a carboxy, or a lower alkoxycarbonyl; a lower alkenyl optionally substituted by a halogen, a hydroxy, a carboxy, or a lower alkoxycarbonyl; a lower alkylthio; an acyl; an acyloxy; a carboxy; a lower alkoxycarbonyl; an amino optionally substituted by a lower alkyl or an acyl; a hydrazino, a nitro; a cyano; a phenyl; or a heterocyclic group; and the broken line is the presence or absence of a bond (hereinafter, ring A is regarded as A-h);

3) a compound wherein R is a hydrogen;

4) a compound wherein Z is oxygen;

5) a compound wherein $Y^1$ and $Y^2$ are independently a hydrogen, a halogen, a lower alkyl or a cyano (hereinafter, $Y^1$ and $Y^2$ are regarded as Y-a);

a compound wherein $Y^1$ and $Y^2$ are independently a hydrogen, or a lower alkyl (hereinafter, $Y^1$ and $Y^2$ are regarded as Y-b);

a compound wherein $Y^1$ and $Y^2$ are a hydrogen (hereinafter, $Y^1$ and $Y^2$ are regarded as Y-c);

6) a compound wherein n is 1 or 2, and all of the broken line are the presence of a bond;

a compound wherein n is 1, and the broken line is the presence of a bond;

7) a compound wherein R is a hydrogen, Z is oxygen, n is 0, and a combination of $Ar^1$ and ring A (Ar1, A) is as follows: (Ar1,A)=(Ar1-a, A-a), (Ar1-a, A-b), (Ar1-a, A-c), (Ar1-b, A-a), (Ar1-b, A-b), (Ar1-b, A-c), (Ar1-c, A-a), (Ar1-c, A-b), (Ar1-c, A-c), (Ar1-d, A-a), (Ar1-d, A-b), (Ar1-d, A-c), (Ar1-e, A-a), (Ar1-e, A-b), (Ar1-e, A-c), (Ar1-a, A-e), (Ar1-a, A-f), (Ar1-a, A-g), (Ar1-b, A-e), (Ar1-b, A-f), (Ar1-b, A-g), (Ar1-c, A-e), (Ar1-c, A-f), (Ar1-c, A-g), (Ar1-d, A-e), (Ar1-d, A-f), (Ar1-d, A-g), (Ar1-e, A-d), (Ar1-e, A-e), (Ar1-e, A-f), (Ar1-e, A-g), (Ar1-e, A-h);

8) a compound wherein R is a hydrogen, Z is oxygen, n is 1 or 2, the broken line is the presence of a bond, and a combination of $Ar^1$, $Y^1$ and $Y^2$, and ring A (Ar1, Y, A) is as follows: (Ar1, Y, A)=(Ar1-a, Y-c, A-a), (Ar1-a, Y-c, A-b), (Ar1-a, Y-c, A-c), (Ar1-b, Y-c, A-a), (Ar1-b, Y-c, A-b), (Ar1-b, Y-c, A-c), (Ar1-c, Y-c, A-a), (Ar1-c, Y-c, A-b), (Ar1-c, Y-c, A-c), (Ar1-d, Y-c, A-a), (Ar1-d, Y-c, A-b), (Ar1-d, Y-c, A-c), (Ar1-e, Y-c, A-a), (Ar1-e, Y-c, A-b), (Ar1-e, Y-c, A-c), (Ar1-e, Y-c, A-d), (Ar1-e, Y-c, A-h) (Ar1-a, Y-b, A-a), (Ar1-a, Y-b, A-b), (Ar1-a, Y-b, A-c) (Ar1-b, Y-b, A-a), (Ar1-b, Y-b, A-b), (Ar1-b, Y-b, A-c), (Ar1-c, Y-b, A-a), (Ar1-c, Y-b, A-b), (Ar1-c, Y-b, A-c), (Ar1-d, Y-b, A-a), (Ar1-d, Y-b, A-b), (Ar1-d, Y-b, A-c), (Ar1-e, Y-b, A-a), (Ar1-e, Y-b, A-b), (Ar1-e, Y-b, A-c), (Ar1-a, Y-c, A-e), (Ar1-a, Y-c, A-f), (Ar1-a, Y-c, A-g), (Ar1-b, Y-c, A-e), (Ar1-b, Y-c, A-f), (Ar1-b, Y-c, A-g), (Ar1-c, Y-c, A-e), (Ar1-c, Y-c, A-f), (Ar1-c, Y-c, A-g), (Ar1-d, Y-c, A-e), (Ar1-d, Y-c, A-f), (Ar1-d, Y-c, A-g), (Ar1-e, Y-c, A-e), (Ar1-e, Y-c, A-f), (Ar1-e, Y-c, A-g), (Ar1-a, Y-b, A-e), (Ar1-a, Y-b, A-f), (Ar1-a, Y-b, A-g), (Ar1-b, Y-b, A-e), (Ar1-b, Y-b, A-f), (Ar1-b, Y-b, A-g), (Ar1-c, Y-b, A-e), (Ar1-c, Y-b, A-f), (Ar1-c, Y-b, A-g), (Ar1-d, Y-b, A-e), (Ar1-d, Y-b, A-f), (Ar1-d, Y-b, A-g), (Ar1-e, Y-b, A-e), (Ar1-e, Y-b, A-f), (Ar1-e, Y-b, A-g), ; and a prodrug thereof, a pharmaceutically acceptable salt or solvate of them.

More preferable compounds are exemplified by the following, which are described in the examples: Ia-1, Ia-3, Ia-4, Ia-5, Ia-6, Ia-7, Ia-9, Ia-10, Ia-16, Ia-17, Ia-18, Ia-23, Ia-27, Ia-29, Ia-30, Ia-37, Ia-38, Ia-39, Ia-42, Ia-44, Ia-45, Ia-46, Ia-48, Ia-53, Ia-54, Ia-55, Ia-59, Ia-60, Ia-61, Ia-62, Ia-63, Ia-64, Ia-69, Ia-72, Ia-95, Ia-97, Ia-104, Ia-105, Ia-112, Ia-113, Ia-118, Ia-119, Ia-144, Ia-145, Ia-146, Ia-150, Ia-152, Ia-153, Ia-156, Ia-161, Ia-162, Ia-177, Ia-204, Ib-01, Ib-3, Ib-4, Ib-6, Ib-7, Ib-8, Ib-9, Ib-11, Ib-12, Ib-13, Ib-14, Ib-144, Ib-17, Ib-18, Ib-19, Ib-20, Ib-24, Ib-25, Ib-26, Ib-28, Ib-35, Ib-73, Ib-97, Ib-102, Ib-105, Ib-131, Ib-137, Id-1, and Id-11.

BEST MODE FOR CARRYING OUT THE INVENTION

Compounds (I) of the invention may be synthesized for example according to Method A to C. Hereinafter, an illustrative preparation is described. Detailed are referred to example in Synthetic Organic Chemistry VI, Japan, 4 (1977) 6, 79, or The 4th series of experimental chemistry (1992) 22, 138.

Method A: A-1+A-2→I

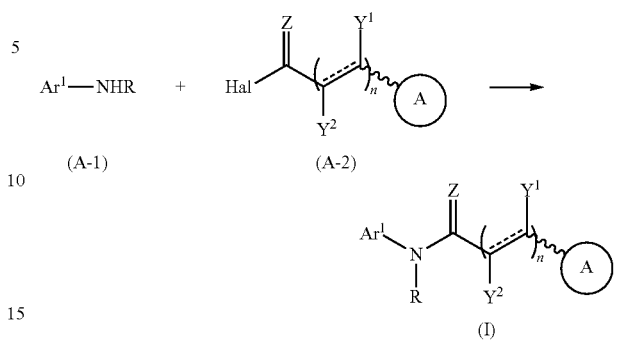

in which Hal is a halogen, and other symbols are as defined above.

The process involves a reaction between amines (A-1) and acid halides (A-2), which leads to compounds (I) in a conventional manner. In general, the reaction may be conducted in the presence of base, e.g., triethylamine, pyridine, excess of (A-1), or dimethylaminopyridine in methylene chloride or tetrahydrofuran as a solvent. The reaction may proceed at a temperature between an ice-cooling and a reflux temperature of the solvent.

Method B: B-1+B-2→I

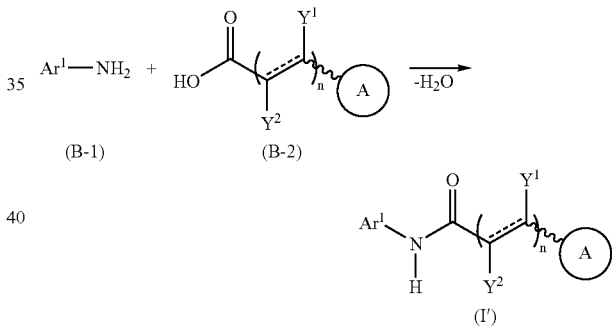

in which the symbols are as defined above.

The process is also a conventional synthesis of amides. In the reaction, amines (B-1) and carboxylic acids (B-2) are directly condensed in the presence of a condensing agent such as dicyclohexylcarbodiimide or 1-ethyl-3-(3-dimethylaminopropyl)carbodiimide hydrochloride to give compounds (I'). The reaction may proceed in a solvent such dimethylformamide, methylene chloride or tetrahydrofuran at a temperature between room temperature and a reflux temperature of the solvent.

Method C: C-1+C-2→I

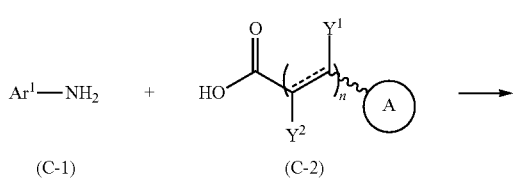

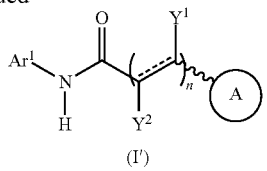

in which the symbols are as defined above.

The process also involves a condensation reaction between amines (C-1) and carboxylic acids (C-2), which may be conducted according to the method as described in Eur. J. Med. Chem., (1994) 29, 841. Specifically, carboxylic acid (C-2) is activated by triphenylphosphine and bromotrichloromethane, and the activated acid is reacted with an amine to give compounds (I'). The reaction may proceed in a solvent such methylene chloride or tetrahydrofuran at a temperature between room temperature and a reflux temperature of the solvent.

Compound (I) wherein R is H as obtained by the method described above may be reacted with a alkyl halide in the presence of sodium hydride in dimethylformamide at a temperature between room temperature to 80° C. to give compound (I) wherein R is a lower alkyl.

Compound (I) wherein Z is sulfur may be obtained by heating compound (I) wherein Z is oxygen in the presence of phosphorus pentasulfide or Lawesson's reagent in a solvent such as pyridine or toluene at a reflux temperature of the solvent.

The method of enhancing the expression of apoAI according to the invention activates a reverse cholesterol transport activity of HDL, an anti-inflammatory activity and an anti-coagulant activity, or the like. As a result, the method of the invention are useful for preventing and/or treating dyslipidemia, arteriosclerotic diseases and various cardiovascular diseases concomitant with them, which are caused by decreased level of HDL in serum. "Dyslipidemia" specifically include conditions of lowered level of serum HDL, hypercholesteremia and hypertriglyceridemia; "arteriosclerotic diseases" specifically include arteriosclerosis, myocardial infarction, and cardiac incompetence; and "various cardiovascular diseases associated with the above diseases" include hyperuricemia, coronary artery diseases, ischaemic heart diseases, corneal opacity, cerebrovascular disease, and hereditary HDL deficiencies (Tangier disease, fish-eye disease).

When a compound of the invention is administered in the method according to the invention, pharmaceutical compositions therefor may be administered either orally or parenterally. For oral routes, the compositions may be formulated conventionally into usual dosage forms such as tablets, tablets, granules, powders, capsules, pills, solutions, syrups, buccals, sublinguals, or the like before administration. For parenteral administration, the compositions may be conventionally formulated into usual dosage forms such as injections, e.g., intramuscular or intravenous injections, suppositories; transdermal patches, inhalation, or the like.

An effective amount of a compound according to the invention may be admixed with various suitable pharmaceutical additives such as excipient, binding agent, wetting agent, disintegrating agent, lubricant, diluent, or the like to give pharmaceutical compositions, if necessary. In the case of injections, the ingredients are sterilized together with a suitable carrier to formulate the composition.

More specifically, the excipients include lactose, sucrose, glucose, starch, calcium carbonate, crystalline cellulose, or the like; the binding agents include methyl cellulose, carboxymethylcellulose, hydroxypropylcellulose, gelatine, polyvinyl pyrrolidone, or the like; the disintegrating agents include carboxymethylcellulose, sodium carboxymethyl cellulose, starch, sodium alginate, algae powder, sodium lauryl sulfate, or the like; the lubricants include talc, magnesium stearate or Macrogol, or the like. Base materials of the suppository may be for example cacao butter, Macrogol, methylcellulose, or the like. Solutions, emulsions or suspensions for injection may comprise a solubilizing agent, a suspending agent, an emulsifying agent, a stabilizing agent, a preserving agent, an isotonic agent, or the like as usually used. Compositions for oral administration may comprise a flavoring agent, an aromatic agent, or the like.

Dose or therapeutically effective amount of the compounds according to the invention for enhancing the expression of apoAI is preferably determined considering age and body weight of patients, sort and severity of diseases to be treated, route of administration, or the like. In the case of oral administration to an adult, the dose range is usually 1 to 100 mg/kg/day, preferably 5 to 30 mg/kg/day. In the case of parenteral administration, the dose differs largely depending on the route of administration, but the dose range is usually 0.1 to 10 mg/kg/day, preferably 1 to 5 mg/kg/day. The dosage unit may be administered to a subject once or several times per day.

Following examples and experiments are presented for purpose of further illustration of the invention, and they are not intended to limit the scope of the invention in any respect.

EXAMPLE 1

4-Chloro-N-(4-tolyl)benzamide (Ib-17)

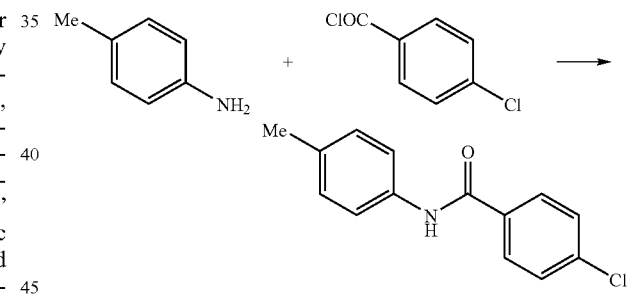

Method A: To a solution of p-toluidine (1.07 g, 10.0 mmol) in chloroform (20 ml) were added pyridine (2.37 g, 30.0 mmol) and then p-chlorobenzoyl chloride (2.63 g, 15.0 mmol) under ice-cooling, and the mixture was stirred at room temperature for 5 hours. After water was added to the reaction, the precipitated solids were collected by filtration, washed sequentially with aqueous saturated sodium hydrogen carbonate, water and chloroform, and then recrystallized from acetone to give Ib-17 (2.0 g, 81.6%).

EXAMPLE 2

Thiophen-2-caroxypyridin-2-yl amide (Ib-122)

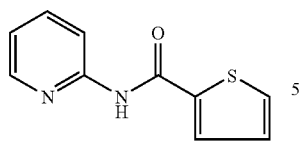

Method C: To a solution of 2-aminopyridine (376 mg, 3.99 mmol), triphenylphosphine (786 mg, 3.00 mmol) and bromotrichloromethane (990 mg, 4.99 mmol) in tetrahydrofuran (10 ml) was added 2-thiophen carboxylic acid (256 mg, 2.00 mmol), and the mixture was heated at reflux for 6 hours, after which the solvent was removed in vacuo. The residue was subjected to silica gel chromatography using ethyl acetate-hexane=1:3 as eluent to give crystals, which were recrystallized from 95% ethanol to give Ib-122 (342 mg, 83.8%).

EXAMPLE 3

N-Methyl-N-phenylbenzamide (Ib-27)

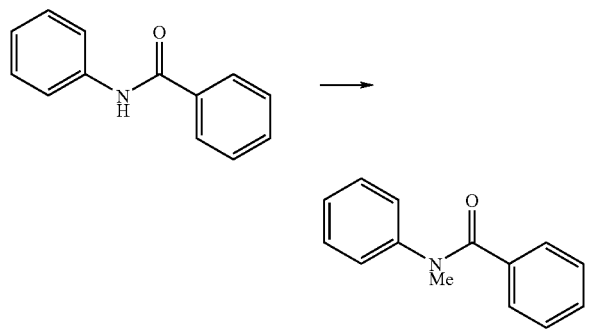

A solution of Ib-1 (180 mg, 0.91 mmol) in dimethylformamide (3 ml) was dropwise added to sodium hydride (60%, 40 mg, 1.00 mmol) under ice-cooling, and the mixture was stirred at room temperature for 30 minutes. To the mixture was added methyl iodide (213 mg, 1.50 mmol), and the reaction was allowed to proceed for 5 hours. After an ice water was added to the reaction, the mixture was extracted with ethyl acetate, and then the extract was washed with water and saturated brine, and dried over anhydrous magnesium sulfate. The solvent was removed in vacuo. The residue was subjected to silica gel chromatography using ethyl acetate-hexane=1:1 as eluent to give Ib-27 (180 mg, 85.3%) as colorless oil.

EXAMPLE 4

3-Phenyl-N-quinoxalin-2-yl-acrylamide (Ia-9)

Method A: To a solution of 2-aminoquinoxaline (435 mg, 3.00 mmol) in tetrahydrofuran (12 ml) were added triethylamine (728 mg, 7.20 mmol) and cinnamoyl chloride (1.20 g, 7.20 mmol) with stirring under ice-cooling, and the reaction was continued for 5 hours, after which the mixture was allowed to stand overnight. After an ice water was added to the reaction, the mixture was extracted with ethyl acetate, and then the extract was washed with water, and dried over anhydrous magnesium sulfate. The solvent was removed in vacuo. The residue was subjected to silica gel chromatography using ethyl acetate-hexane=1:2 as eluent, followed by recrystallization from ethyl acetate-hexane to give Ia-9 (128 mg, 15.5%).

EXAMPLE 5

3-Pyridin-3-yl-N-pyridin-2-yl-acrylamide (Ia-112)

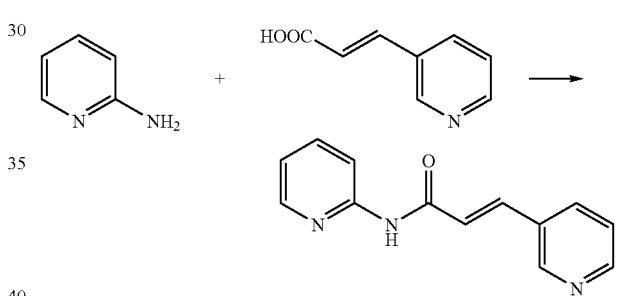

Method B: To a solution of 2-aminopyridine (0.986 g, 10.48 mmol) and β-(3-pyridyl)acrylic acid (0.746 g, 5.00 mmol) in tetrahydrofuran (10 ml) was added 1-ethyl-3-(3-dimethylaminopropyl)carbodiimide hydrochloride (1.006 g, 5.25 mmol), and the mixture was stirred for 21 hours, then the solvent was removed in vacuo. To the residue was added a 10% citric acid aqueous solution, and the mixture was extracted with chloroform. The extract was washed with water, aqueous saturated sodium hydrogen carbonate and water, dried over anhydrous magnesium sulfate. The solvent was removed in vacuo. The residue was purified by silica gel chromatography using ethyl acetate-hexane=1:1, followed by recrystallization from ethyl acetate-chloroform (1:1) to give Ia-112 (440 mg, 39.0%).

EXAMPLE 6

3-Furan-2-yl-N-pyridin-2-yl-acrylamide (Ia-104)

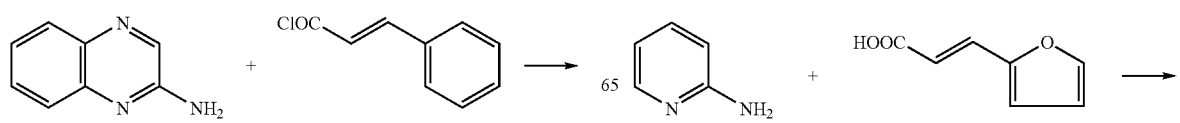

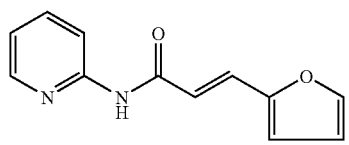

Method C: To a solution of 2-aminopyridine (376 mg, 4.00 mmol), triphenylphosphine (786 mg, 3.00 mmol) and bromotrichloromethane (990 mg, 4.99 mmol) in tetrahydrofuran (10 ml) was added 2-furan acrylic acid (276 mg, 2.00 mmol), and the mixture was heated at reflux for 6 hours, after which the solvent was removed in vacuo. The residue was subjected to silica gel chromatography using ethyl acetate-hexane=1:2 as eluent to give crystals, which were then recrystallized from 95% ethanol to give Ia-104 (243 mg, 56.8%).

In a similar manner, other compounds were prepared, of which chemical structures are shown in the following tables

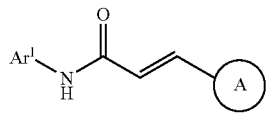

TABLE 1-continued

| No. | Ar¹ | A |
|---|---|---|
| Ia-19 | quinoxalin-2-yl | 4-methylphenyl |
| Ia-20 | 2,7-dimethyl-1,8-naphthyridin-3-yl | pyridin-3-yl |
| Ia-21 | benzoxazol-2-yl | 1-methyl-pyrrol-2-yl |
| Ia-22 | pyridin-2-yl | 6-methylpyridin-3-yl |
| Ia-23 | pyridin-2-yl | 3,4-dimethylphenyl |
| Ia-24 | pyridin-2-yl | 2,4,6-trimethylphenyl |
| Ia-25 | pyridin-2-yl | 4-isopropylphenyl |
| IA-26 | pyridin-2-yl | 6-methylpyridin-3-yl |
| Ia-27 | 6-methylpyridin-2-yl | pyridin-3-yl |
| Ia-28 | 2-methylquinolin-3-yl | 2,4,6-trimethylphenyl |
| Ia-29 | pyridin-2-yl | 2,4-dimethoxyphenyl |
| Ia-30 | pyridin-2-yl | 4-(trifluoromethyl)phenyl |
| Ia-31 | 6-chloropyridin-2-yl | 4-(trifluoromethyl)phenyl |
| Ia-32 | 6-methylpyridin-2-yl | 4-(trifluoromethyl)phenyl |
| Ia-33 | 6-aminopyridin-2-yl | 4-(trifluoromethyl)phenyl |
| Ia-34 | pyridin-2-yl | 3-(trifluoromethyl)phenyl |
| Ia-35 | pyridin-2-yl | 2-(trifluoromethyl)phenyl |
| Ia-36 | quinoxalin-2-yl | 4-(trifluoromethyl)phenyl |

TABLE 2

| No. | Ar¹ | A |
|---|---|---|
| Ia-37 | pyridin-2-yl | 2-chloropyridin-3-yl |

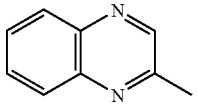

TABLE 2-continued

Ia

No. | Ar¹ | A
--- | --- | ---
Ia-38 | 2-pyridyl | 3-chlorophenyl
Ia-39 | 2-pyridyl | 4-chlorophenyl
Ia-40 | 2-pyridyl | 3,4-dichlorophenyl
Ia-41 | 2-quinoxalinyl | 4-chlorophenyl
Ia-42 | 2-pyridyl | 6-chloropyridin-3-yl
Ia-43 | 2-pyridyl | 2-chloro-4-methylpyridin-5-yl
Ia-44 | 2-pyridyl | 4-fluorophenyl
Ia-45 | 2-pyridyl | 3-fluorophenyl
Ia-46 | 2-pyridyl | 2-fluorophenyl
Ia-47 | 2-quinoxalinyl | 4-fluorophenyl
Ia-48 | 2-pyridyl | 6-fluoropyridin-3-yl
Ia-49 | 2-pyridyl | 3-fluoro-4-methoxyphenyl
Ia-50 | 2-pyridyl | 3,5-difluoro-4-methoxyphenyl
Ia-51 | 2-pyridyl | 4-hydroxyphenyl
Ia-52 | 3-quinolinyl | 4-hydroxyphenyl
Ia-53 | 2-pyridyl | 3,4-diethoxyphenyl
Ia-54 | 2-pyridyl | 3-methoxyphenyl
Ia-55 | 2-pyridyl | 3,4-dimethoxyphenyl
Ia-56 | 6-chloropyridin-2-yl | 3,4-dimethoxyphenyl
Ia-57 | 2,6-dimethyl-4-pyridyl | 3,4-dimethoxyphenyl
Ia-58 | 2-pyridyl | 2,5-dimethyl-4,5-dimethoxyphenyl TABLE 2-continued Ia structure: Ar¹-NH-C(=O)-CH=CH-A

| No. | Ar¹ | A |
|---|---|---|
| Ia-59 | 2-pyridyl | 2,4-dimethoxyphenyl (OMe at 1,4 positions) |
| Ia-60 | 2-pyridyl | 3,5-dimethoxyphenyl |
| Ia-61 | phenyl | 2,3-dimethoxyphenyl |
| Ia-62 | phenyl | 3,4-dimethoxyphenyl |
| Ia-63 | phenyl | 2,4-dimethoxyphenyl |
| Ia-64 | 4-methoxyphenyl | 2,3-dimethoxyphenyl |
| Ia-65 | 4-methoxyphenyl | 3,4-dimethoxyphenyl |
| Ia-66 | 2-quinolinyl | 3,4-dimethoxyphenyl |
| Ia-67 | 2-pyridyl | 3-OMe, 4-OAc phenyl |
| Ia-68 | 2-pyridyl | 3-OH, 4-OMe phenyl |

TABLE 3

Ia structure: Ar¹-NH-C(=O)-CH=CH-A

| No. | Ar¹ | A |
|---|---|---|
| Ia-69 | 2-pyridyl | 3,4,5-trimethoxyphenyl |
| Ia-70 | 2-pyridyl | 3,4,5-trimethoxyphenyl (alt arrangement) |
| Ia-71 | 2-pyridyl | 3,5-di-OMe, 4-OnPr phenyl |
| Ia-72 | 2-pyridyl | 3,5-di-OMe, 4-OH phenyl |
| Ia-74 | 2-pyridyl | 3,4-di-OMe, 5-OH phenyl |
| Ia-75 | 2,7-dimethyl-1,8-naphthyridinyl | 3,4,5-trimethoxyphenyl |

TABLE 3-continued
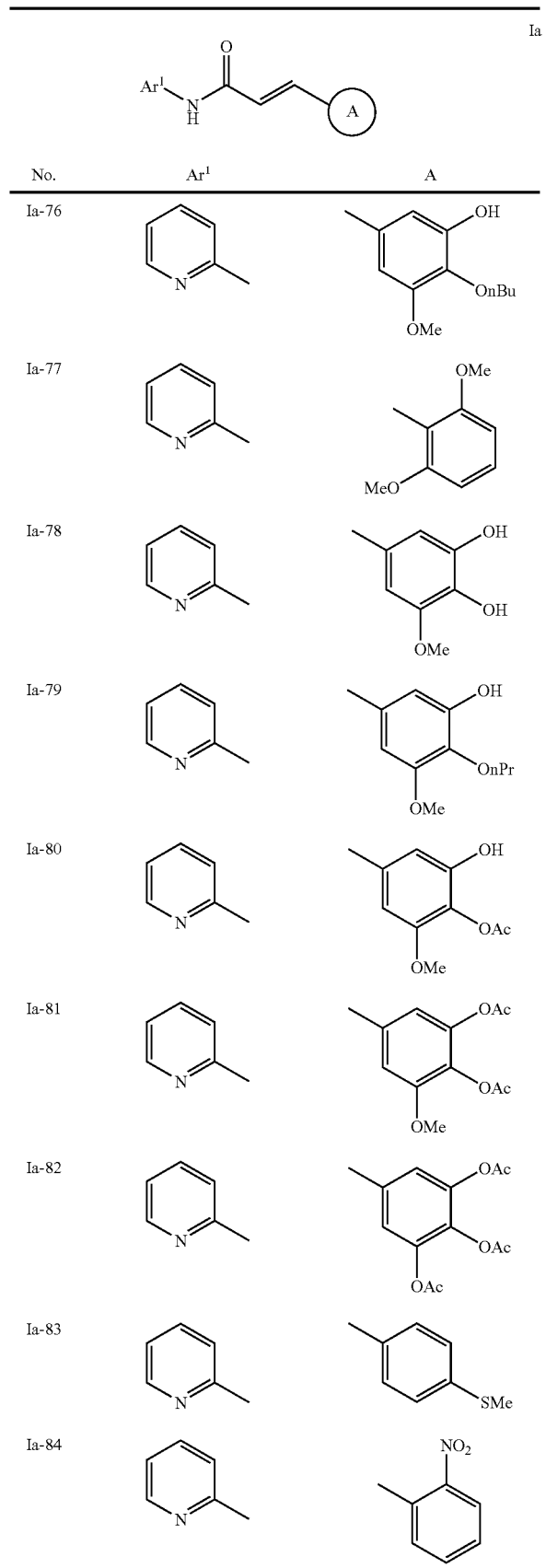
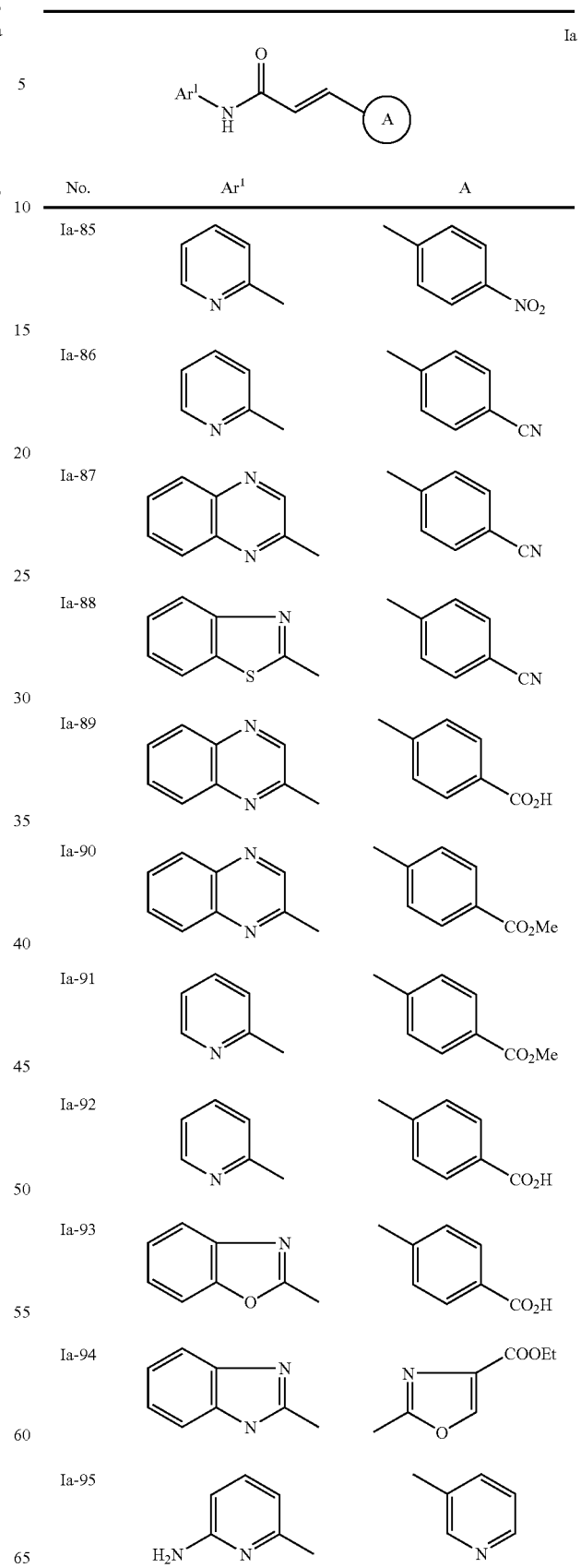

TABLE 3-continued

Ia

| No. | Ar¹ | A |
|---|---|---|
| Ia-96 | 2-pyridyl | 4-aminophenyl |
| Ia-97 | 2-pyridyl | 5-methyl-2-(NHMe)pyridyl |
| Ia-98 | 2-pyridyl | 4-(NMe₂)phenyl |
| Ia-99 | 2-benzothiazolyl | 4-(NMe₂)phenyl |
| Ia-100 | 2-pyridyl | 4-(NHAc)phenyl |
| Ia-101 | 2-benzoxazolyl | 4-(NMe₂)phenyl |
| Ia-102 | 2-quinoxalinyl | 4-(NHAc)phenyl |
| Ia-103 | 2-quinoxalinyl | 4-(NMe₂)phenyl |

TABLE 4

Ia

| No. | Ar¹ | A |
|---|---|---|
| Ia-104 | 2-pyridyl | 5-methyl-2-furyl |
| Ia-105 | 2-pyridyl | 2-methyl-thienyl |
| Ia-106 | 2-pyridyl | 2,3-dimethylthienyl |
| Ia-107 | 4-pyridyl | 3-furyl |
| Ia-108 | 2-pyridyl | methylpyrazolyl |
| Ia-109 | 2-pyrazinyl | methylfuryl |
| Ia-110 | 2-pyridyl | methylpyrrolyl |
| Ia-111 | 2-pyridyl | 1-methyl-pyrrolyl |
| Ia-112 | 2-pyridyl | methylpyridyl |
| Ia-113 | 2-pyridyl | 2-methylpyridyl |
| Ia-114 | 2-pyridyl | methylthiazolyl |
| Ia-115 | 2-pyridyl | methyloxazolyl |
| Ia-116 | 2-pyridyl | methylisoxazolyl |

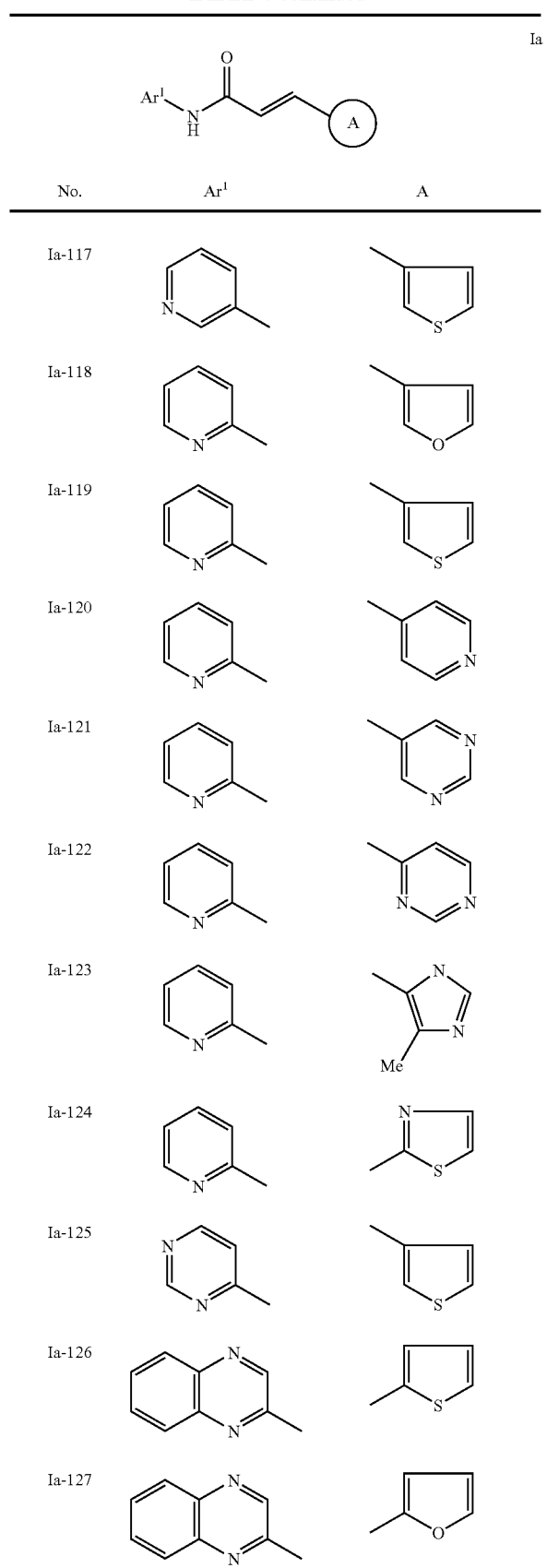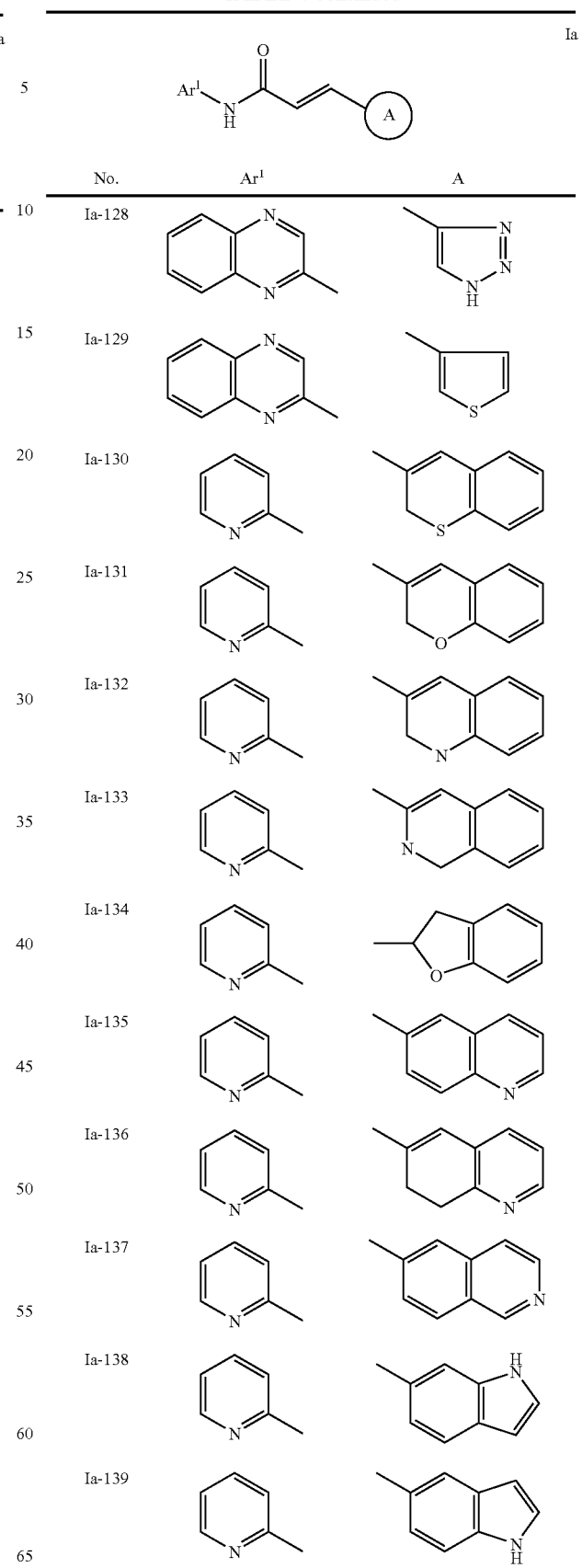

TABLE 4-continued

| No. | Ar¹ | A |
|---|---|---|
| Ia-140 | 2-pyridyl | 5-benzimidazolyl |
| Ia-141 | 2-pyridyl | 5-benzothienyl |
| Ia-142 | 2-pyridyl | 5-benzofuranyl |
| Ia-143 | 2-pyridyl | 6-benzofuranyl |

TABLE 5

| No. | Ar¹ | A |
|---|---|---|
| Ia-144 | phenyl | 4-MeO-phenyl |
| Ia-145 | phenyl | 3-MeO-phenyl |
| Ia-146 | phenyl | 2-MeO-phenyl |
| Ia-147 | 2-pyridyl | 5-MeO-2-pyridyl |
| Ia-148 | 2-pyridyl | 2-MeO-4-pyridyl |
| Ia-149 | 2-pyridyl | 4-MeO-2-pyridyl |
| Ia-150 | 5-pyridyl | 2-MeO-5-pyridyl |
| Ia-151 | 4-MeO-phenyl | 4-MeO-phenyl |
| Ia-152 | 2-pyridyl | 3-MeO-phenyl |
| Ia-153 | 2-pyridyl | 4-MeO-phenyl |
| Ia-154 | 2-benzoxazolyl | 4-MeO-phenyl |
| Ia-155 | 2-quinolyl | 4-MeO-phenyl |
| Ia-156 | 2-pyridyl | 2-MeO-phenyl |
| Ia-157 | 2-benzimidazolyl | 2,4-diMeO-phenyl |
| Ia-158 | 2-quinoxalinyl | 4-MeO-phenyl |
| Ia-159 | 2-pyridyl | 6-MeO-2-quinolyl |

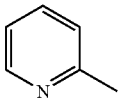

TABLE 5-continued and TABLE 6 contain chemical structure entries Ia-160 through Ia-178, which are not transcribable as text.

TABLE 6-continued
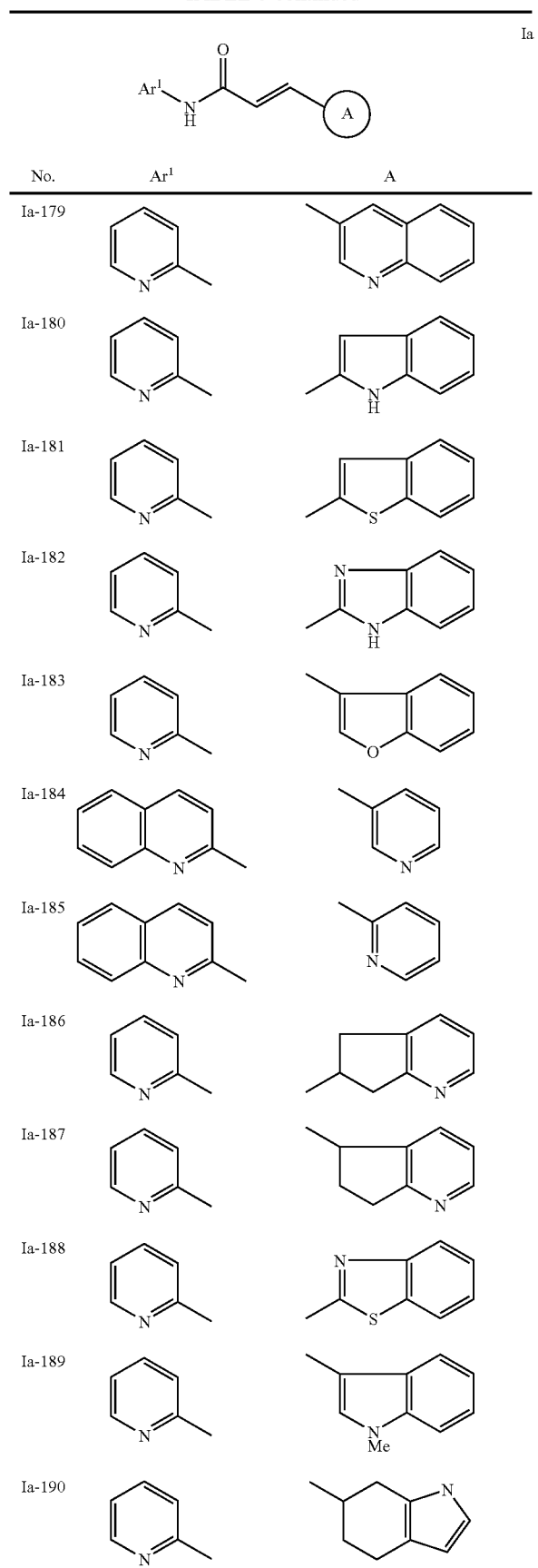
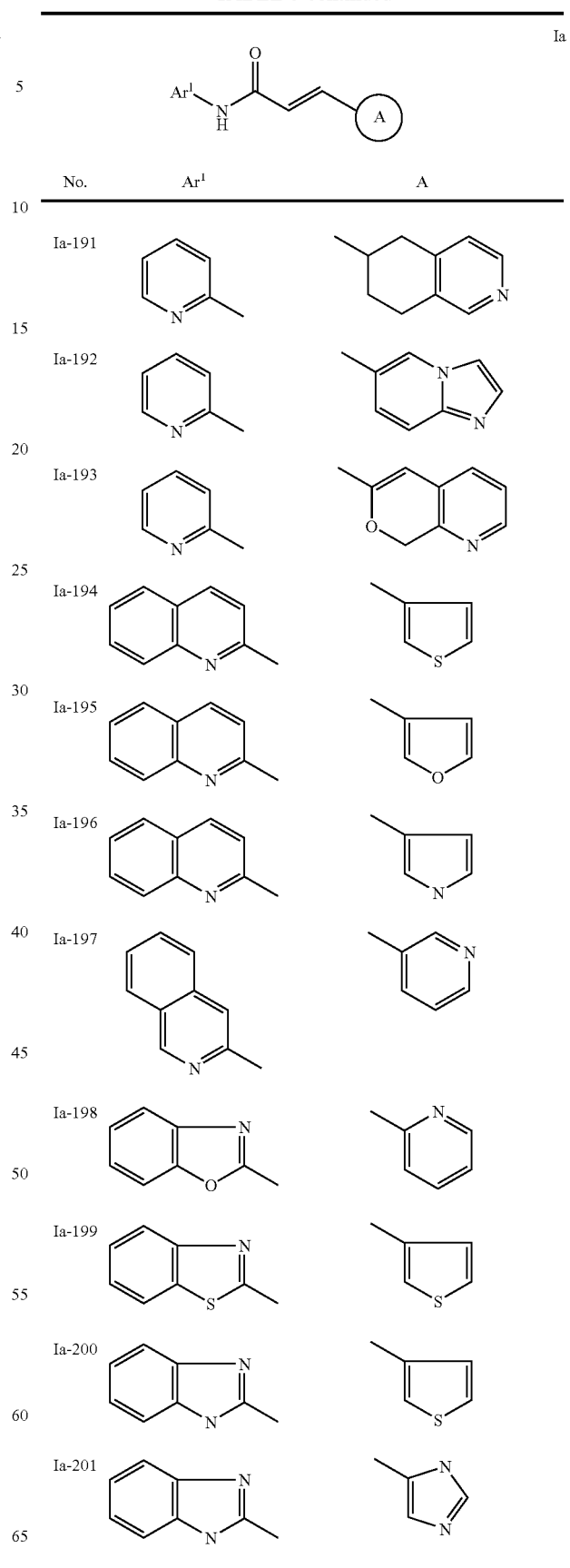

TABLE 6-continued

| No. | Ar¹ | A |
|---|---|---|
| Ia-202 | 7-azaindole-2-yl | furan-3-yl |
| Ia-203 | 1,3,4-thiadiazol-2-yl | pyridin-3-yl |
| Ia-204 | thiazol-2-yl | pyridin-3-yl |
| Ia-205 | quinoxalin-2-yl | biphenyl-4-yl |
| Ia-206 | quinoxalin-2-yl | 4-phenoxyphenyl |
| Ia-207 | quinoxalin-2-yl | 2H-chromen-3-yl |
| Ia-208 | quinoxalin-2-yl | benzothiophen-6-yl |
| Ia-209 | quinoxalin-2-yl | 1H-pyrrol-3-yl |

TABLE 7

| No. | Ar¹ | R (*1) | A |
|---|---|---|---|
| Ib-1 | phenyl | | phenyl |
| Ib-2 | phenyl | | 2-ethoxyphenyl |
| Ib-3 | phenyl | | benzofuran-2-yl |
| Ib-4 | 4-methylphenyl | | 2-methylphenyl |
| Ib-5 | 4-methylphenyl | | 2-methoxyphenyl |
| Ib-6 | 4-methylphenyl | | 2-chlorophenyl |
| Ib-7 | 4-methylphenyl | | 3-methylphenyl |
| Ib-8 | 4-methylphenyl | | 3-methoxyphenyl |
| Ib-9 | 4-methylphenyl | | 3-chlorophenyl |
| Ib-10 | 4-methylphenyl | | naphthalen-1-yl |
| Ib-11 | 4-methylphenyl | | 4-methylphenyl |

TABLE 7-continued

Ib structure: Ar¹-N(R)-C(=O)-A

| No. | Ar¹ | R (*1) | A |
|-----|-----|--------|---|
| Ib-12 | 4-Me-C₆H₄ | | 4-Me-C₆H₄-CHO |
| Ib-13 | 4-Me-C₆H₄ | | 4-Me-C₆H₄-CO₂Me |
| Ib-14 | 4-Me-C₆H₄ | | 4-Me-C₆H₄-CO₂H |
| Ib-15 | 4-Me-C₆H₄ | | 4-Me-C₆H₄-CH=CH-CO₂Et |
| Ib-16 | 4-Me-C₆H₄ | | 4-Me-C₆H₄-CH=CH-CO₂H |
| Ib-17 | Ph | | 4-Cl-C₆H₄ |
| Ib-18 | 4-Me-C₆H₄ | | 4-OMe-C₆H₄ |
| Ib-19 | 4-Me-C₆H₄ | | 4-OEt-C₆H₄ |
| Ib-20 | 4-Me-C₆H₄ | | 2-naphthyl |
| Ib-21 | 4-F₃C-C₆H₄ | | 4-CF₃-C₆H₄ |
| Ib-22 | 4-i-Pr-C₆H₄ | | 4-i-Pr-C₆H₄ |
| Ib-23 | 4-i-Pr-C₆H₄ | | 4-(4-Me-C₆H₄)-1,2,3-thiadiazol-5-yl |
| Ib-24 | 4-MeO-C₆H₄ | | Ph |
| Ib-25 | 4-EtO-C₆H₄ | | 4-Me-C₆H₄ |
| Ib-26 | 4-Cl-C₆H₄ | | 4-Me-C₆H₄ |
| Ib-27 | Ph | Me | Ph |
| Ib-28 | 4-Cl-C₆H₄ | | 4-Cl-C₆H₄ |
| Ib-29 | 4-Me-C₆H₄ | | 4-biphenyl |
| Ib-30 | 4-MeO-C₆H₄ | | 4-biphenyl |
| Ib-31 | Ph | | 4-oxo-4H-chromen-2-yl |
| Ib-32 | Ph | | quinolin-7-yl |

(*1) R is H unless otherwise noted

TABLE 8

Structure Ib: Ar¹-N(R)-C(=O)-A

| No. | Ar¹ | R (*1) | A |
|---|---|---|---|
| Ib-33 | 2-pyridyl | | 2-naphthyl |
| Ib-34 | 2-pyridyl | | 1-naphthyl |
| Ib-35 | 2-pyridyl | | 4-biphenyl |
| Ib-36 | 2-pyridyl | | 6-(1,2,3,4-tetrahydronaphthyl) |
| Ib-37 | 2-pyridyl | | 2-(1,2,3,4-tetrahydronaphthyl) |
| Ib-38 | 2-pyridyl | | phenyl |
| Ib-39 | 2-pyridyl | | 4-(CO₂Me)phenyl |
| Ib-40 | 2-pyridyl | | 4-(CO₂H)phenyl |
| Ib-41 | 2-pyridyl | | 4-CN-phenyl |
| Ib-42 | 2-pyridyl | | 4-F-phenyl |
| Ib-43 | 2-pyridyl | | 4-NHAc-phenyl |
| Ib-44 | 2-pyridyl | | 4-NMe₂-phenyl |
| Ib-45 | 2-pyridyl | | 4-CF₃-phenyl |
| Ib-46 | 2-pyridyl | | 3-CF₃-phenyl |
| Ib-47 | 2-pyridyl | | 2-NO₂-phenyl |
| Ib-48 | 2-pyridyl | | 4-NO₂-phenyl |
| Ib-49 | 2-pyridyl | | 4-Cl-phenyl |
| Ib-50 | 2-pyridyl | | 3-F-phenyl |
| Ib-51 | 2-pyridyl | | 2-Me-phenyl |
| Ib-52 | 2-pyridyl | | 3-Me-phenyl |
| Ib-53 | 2-pyridyl | | 4-Me-phenyl |
| Ib-54 | 2-pyridyl | | 2,4-diMe-phenyl |

TABLE 8-continued
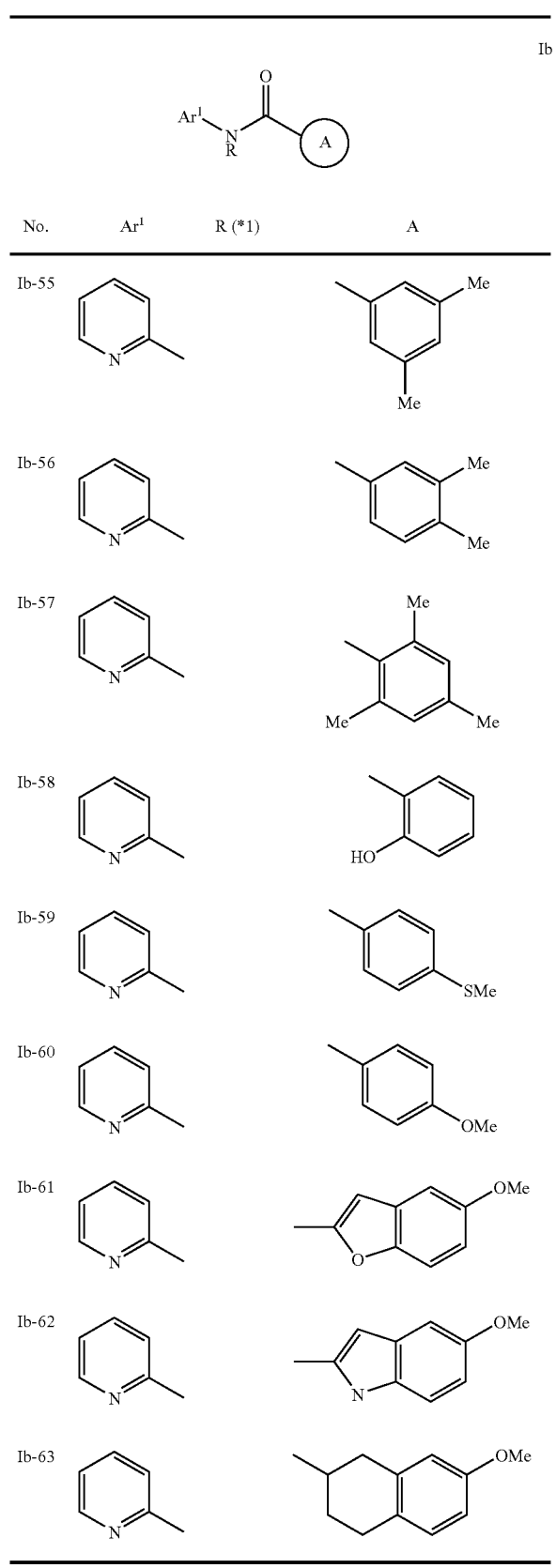
TABLE 9
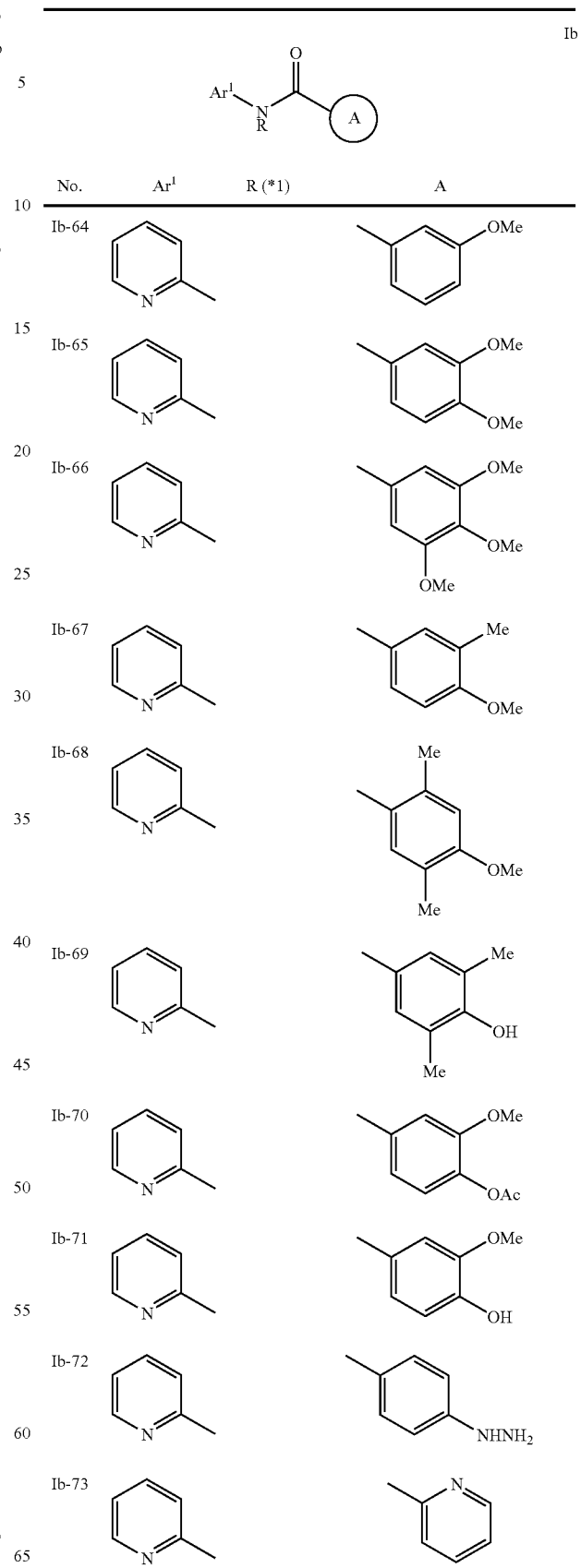
(*1) R is H unless otherwise noted TABLE 9-continued TABLE 9-continued
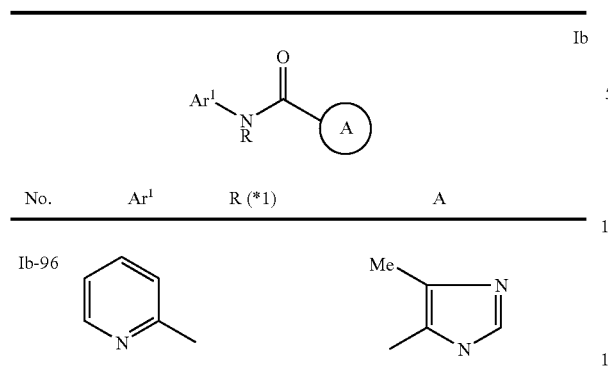
TABLE 10
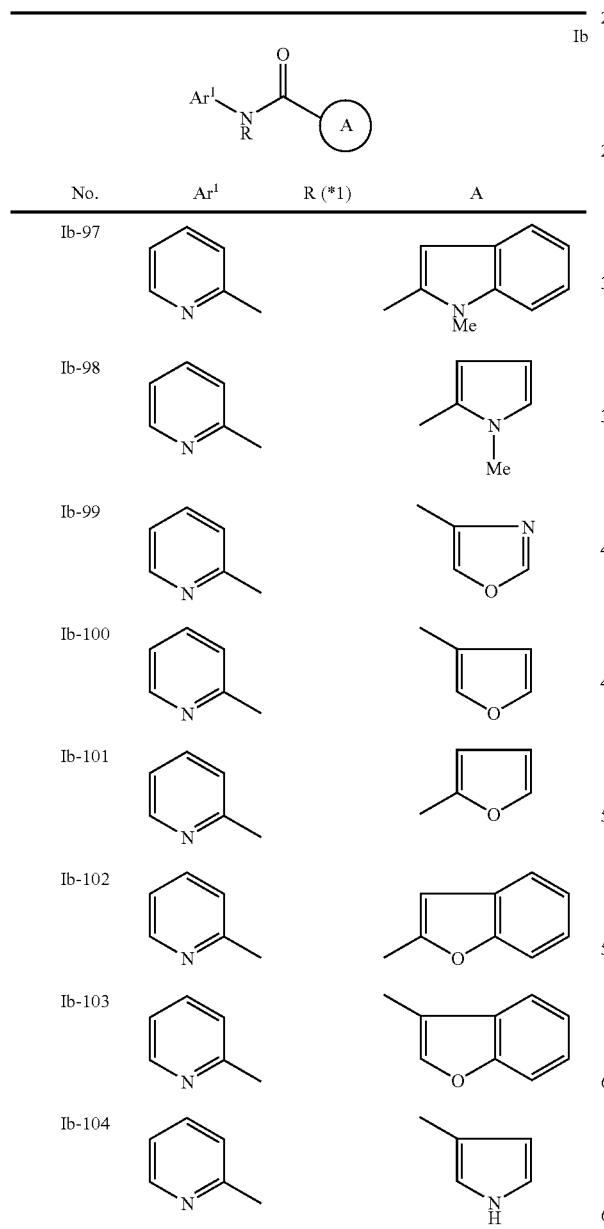
TABLE 10-continued
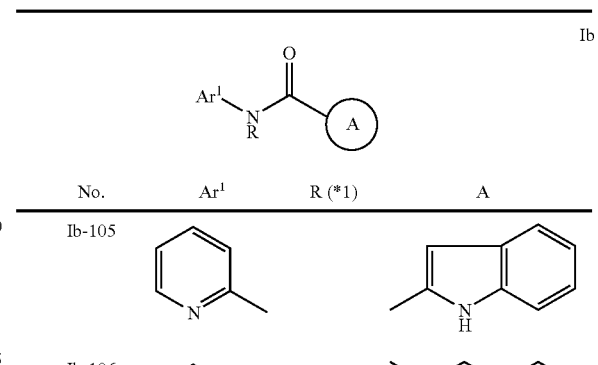
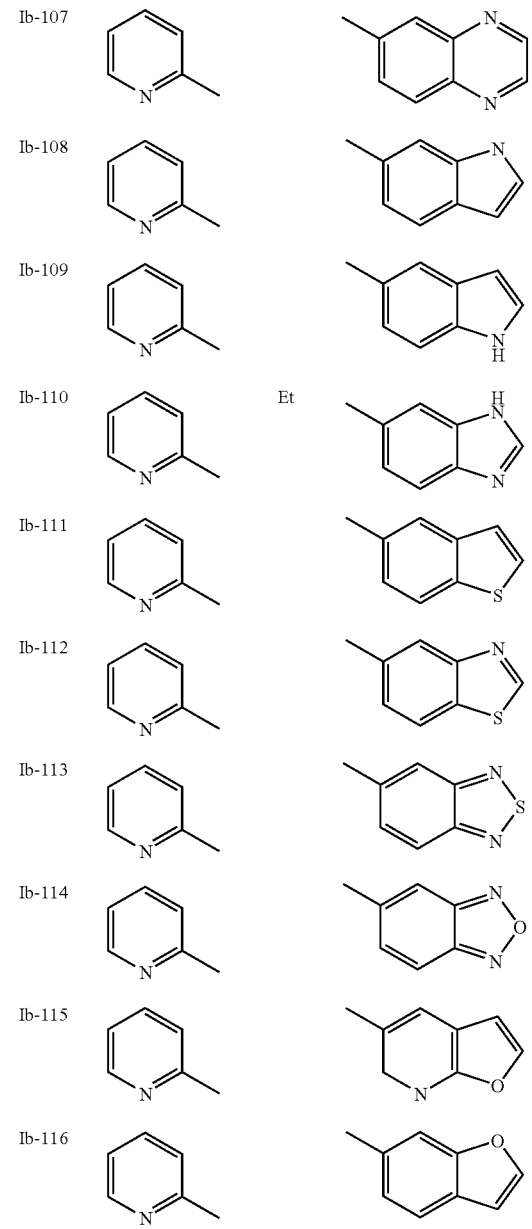

TABLE 10-continued

| No. | Ar¹ | R (*1) | A |
|---|---|---|---|
| Ib-117 | 2-pyridyl | | 3-quinolinyl |
| Ib-118 | 2-pyridyl | | 2-methylquinolin-8-yl |
| Ib-119 | 2-pyridyl | Me | 1,3-dimethylindol-2-yl |
| Ib-120 | 2-pyridyl | | 2-benzimidazolyl |
| Ib-121 | 2-pyridyl | | 4-methylthiazol-5-yl |
| Ib-122 | 2-pyridyl | | 2-methylthien-3-yl |
| Ib-123 | 2-pyridyl | | 2-methylbenzothien-3-yl |
| Ib-124 | 2-pyridyl | | 3-methylthien-2-yl |
| Ib-125 | 2-pyridyl | | 2,3-dimethylthien-4-yl |
| Ib-126 | 2-pyridyl | | 2-methylthiazol-4-yl |
| Ib-127 | 2-pyridyl | | 2-methylbenzothiazol-3-yl |
| Ib-128 | 2-pyridyl | | 3-methyl-2H-chromen-4-yl |
| Ib-129 | 2-pyridyl | | 4-chloro-3-methyl-2H-thiochromen-? |

(*1) R is H unless otherwise noted

TABLE 11

| No. | Ar¹ | R (*1) | A |
|---|---|---|---|
| Ib-130 | 2-methyl-5-phenyl-1,3,4-oxadiazol | | 3-pyridyl |
| Ib-131 | 5-(furan-2-yl)-2-methyl-1,3,4-thiadiazol | | phenyl |

TABLE 11-continued

| No. | Ar¹ | R (*1) | A |
|---|---|---|---|
| Ib-132 | 3-MeO-phenyl-(5-methyl-1,3,4-oxadiazol-2-yl) | | 3-pyridyl |
| Ib-133 | 2-furyl-(5-methyl-1,3,4-oxadiazol-2-yl) | | phenyl |
| Ib-134 | pyrimidin-4-yl | | 3-thienyl |
| Ib-135 | pyrazin-2-yl | | 3-thienyl |
| Ib-136 | 1H-indol-2-yl | | 2-thienyl |
| Ib-137 | quinoxalin-2-yl | | phenyl |
| Ib-138 | quinoxalin-2-yl | Me | 4-methylphenyl |
| Ib-139 | quinoxalin-2-yl | | 4-(CO₂Me)phenyl |
| Ib-140 | quinoxalin-2-yl | | 3,4,5-tri(OMe)phenyl |
| Ib-141 | quinoxalin-2-yl | | 4-CN-phenyl |
| Ib-142 | quinoxalin-2-yl | | 4-F-phenyl |

TABLE 11-continued
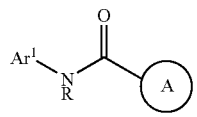
| No. | Ar¹ | R (*1) | A |
|---|---|---|---|
| Ib-143 | quinoxalin-2-yl | | 4-Br-C₆H₄ |
| Ib-144 | quinoxalin-2-yl | | 4-Cl-C₆H₄ |
| Ib-145 | quinoxalin-2-yl | | 4-OMe-C₆H₄ |
| Ib-146 | quinoxalin-2-yl | | 4-OH-C₆H₄ |
| Ib-147 | quinoxalin-2-yl | | 4-NH₂-C₆H₄ |
| Ib-148 | quinoxalin-2-yl | | 4-NHAc-C₆H₄ |
| Ib-149 | quinoxalin-2-yl | | 4-NMe₂-C₆H₄ |
| Ib-150 | quinoxalin-2-yl | | 4-biphenyl |
| Ib-151 | quinoxalin-2-yl | | 4-PhO-C₆H₄ |
| Ib-152 | quinoxalin-2-yl | | 2-naphthyl |
| Ib-153 | quinoxalin-2-yl | Me | benzo[b]thiophen-6-yl |

TABLE 11-continued

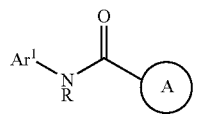
Ib

| No. | Ar¹ | R (*1) | A |
|---|---|---|---|
| Ib-154 | quinoxalin-2-yl-methyl | | 2-furyl-methyl |
| Ib-155 | quinoxalin-2-yl-methyl | | 3-furyl-methyl |
| Ib-156 | quinoxalin-2-yl-methyl | | 2-thienyl-methyl |
| Ib-157 | quinoxalin-2-yl-methyl | | 3-thienyl-methyl |
| Ib-158 | quinoxalin-2-yl-methyl | | 1H-pyrrol-3-yl-methyl |
| Ib-159 | quinoxalin-2-yl-methyl | | 1H-1,2,3-triazol-4-yl-methyl |
| Ib-160 | quinoxalin-2-yl-methyl | | benzothiazol-5-yl-methyl |
| Ib-161 | quinoxalin-2-yl-methyl | | pyridin-3-yl-methyl |
| Ib-162 | quinoxalin-2-yl-methyl | | pyridin-4-yl-methyl |
| Ib-163 | quinoxalin-2-yl-methyl | | naphthalen-2-yl-methyl |

(*1) R is H unless otherwise noted

TABLE 12

Structure: Ar¹-N(R)-C(=O)-A (Ib)

| No. | Ar¹ | R (*1) | A |
|---|---|---|---|
| Ib-164 | quinolin-2-yl | | phenyl |
| Ib-165 | quinolin-2-yl | | 4-chlorophenyl |
| Ib-166 | quinolin-2-yl | | 4-methoxyphenyl |
| Ib-167 | quinolin-2-yl | Et | 3-(O(CH₂)₃CO₂Et)phenyl |
| Ib-168 | quinolin-2-yl | | 3-(O(CH₂)₃CO₂H)phenyl |
| Ib-169 | quinolin-2-yl | | 4-biphenyl |
| Ib-170 | 4-Me-quinolin-2-yl | | 4-biphenyl |
| Ib-171 | quinolin-2-yl | | 4-(pyrrol-2-yl)phenyl |
| Ib-172 | quinolin-2-yl | | thiophen-3-yl |
| Ib-173 | quinolin-2-yl | | furan-2-yl |
| Ib-174 | quinolin-2-yl | | pyrrol-3-yl |
| Ib-175 | isoquinolin-3-yl | | pyridin-3-yl |
| Ib-176 | quinolin-3-yl | | phenyl |
| Ib-177 | benzimidazol-2-yl | | 4-biphenyl |
| Ib-178 | benzimidazol-2-yl | | 4-methoxyphenyl |
| Ib-179 | benzimidazol-2-yl | | thiophen-3-yl |
| Ib-180 | benzimidazol-2-yl | | imidazol-4-yl |
| Ib-181 | benzimidazol-2-yl | | 2-methyl-4-(COOEt)oxazol-5-yl |
| Ib-182 | benzoxazol-2-yl | | 4-(NMe₂)phenyl |
| Ib-183 | benzoxazol-2-yl | | 4-methylphenyl |
| Ib-184 | benzoxazol-2-yl | | 4-(CO₂H)phenyl |

TABLE 12-continued

Ib

![structure: Ar¹-N(R)-C(=O)-A]

(*1) R is H unless otherwise noted

| No. | Ar¹ | R (*1) | A |
|---|---|---|---|
| Ib-185 | benzoxazol-2-yl | | N-methylpyrrol-2-yl |
| Ib-186 | benzoxazol-2-yl | | pyridin-2-yl |
| Ib-187 | benzoxazol-2-yl | | 4-methoxyphenyl |
| Ib-188 | benzothiazol-2-yl | | phenyl |
| Ib-189 | benzothiazol-2-yl | | 4-NMe₂-phenyl |
| Ib-190 | benzothiazol-2-yl | | 4-CN-phenyl |
| Ib-191 | benzothiazol-2-yl | | thiophen-3-yl |
| Ib-192 | benzothiazol-2-yl | | benzothiazol-2-yl |

TABLE 13

Ic

![structure: Ar¹-NH-C(=O)-CH=CH-A with wavy bond]

| No. | Ar¹ | A | Dashed lines | Bond |
|---|---|---|---|---|
| Ic-1 | phenyl | 2-methoxyphenyl | cis | presence |
| Ic-2 | phenyl | phenyl | cis | presence |
| Ic-3 | pyridin-2-yl | pyridin-2-yl | cis | presence |
| Ic-4 | pyridin-2-yl | furan-3-yl | cis | presence |
| Ic-5 | phenyl | phenyl | | absence |

TABLE 13-continued

Id

![structure: Ar¹-NH-C(=O)-CH=CH-CH=CH-A]

| No. | Ar¹ | A |
|---|---|---|
| Id-1 | pyridin-2-yl | phenyl |
| Id-2 | pyridin-2-yl | pyridin-3-yl |
| Id-3 | phenyl | 4-methylphenyl |
| Id-4 | phenyl | thiophen-3-yl |
| Id-5 | pyridin-2-yl | 3,4,5-trimethoxyphenyl |
| Id-6 | pyridin-2-yl | furan-3-yl |
| Id-7 | pyridin-2-yl | thiophen-3-yl |
| Id-8 | pyridin-2-yl | 3,4-dimethoxyphenyl |

TABLE 13-continued

| | | | |
|---|---|---|---|
| Id-9 | 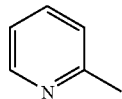 | 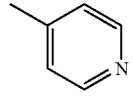 | 5 |
| Id-10 | 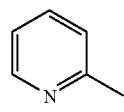 | 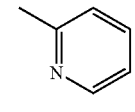 | |

TABLE 14

| Compound | m.p (° C.) | Molecular formula | Elemental analysis (Calculated) | Elemental analysis (Found) | NMR |
|---|---|---|---|---|---|
| Ia-1 | 153-155 | C15H13NO | C, 80.69; H, 5.87; N, 6.27 | C, 80.86; H, 5.91; N, 6.36 | 6.56 (1H, d, J = 15.3), 7.13 (1H, t, J = 7.5), 7.26-7.39 (5H, m), 7.46 (1H, brs), 7.50-7.54 (2H, m), 7.62 (2H, brd, J = 7.5), 7.76 (1H, d, J = 15.3) |
| Ia-2 | 119-120 | C17H17NO3 | C, 72.07; H, 6.05; N, 4.94 | C, 72.06; H, 6.02; N, 5.00 | 3.81 (3H, s), 3.89 (3H, s), 6.50-6.61 (3H, m), 7.36-7.44 (3H, m), 7.53-7.59 (2H, m), 6.69-7.77 (2H, m), 8.41 (1H, brm) |
| Ia-3 | 117-118 | C16H15NO2 | C, 75.87; H, 5.97; N, 5.53 | C, 75.97; H, 5.93; N, 5.49 | 3.82 (3H, s), 6.55 (1H, d, J = 15.6), 6.69 (1H, m), 7.06 (1H, m), 7.24 (1H, t, J = 8.0), 7.36-7.55 (8H, m), 7.76 (1H, d, J = 15.6) |
| Ia-4 | 154-156 | C16H15NO2 | C, 75.87; H, 5.97; N, 5.53 | C, 76.01; H, 6.02; N, 5.59 | 3.80 (3H, s), 6.54 (1H, d, J = 15.6), 6.88 (2H, d, J = 9.2), 7.35-7.55 (8H, m), 7.74 (1H, d, J = 15.6) |
| Ia-5 | 195-196 | C13H11N3O | C, 69.32; H, 4.92; N, 18.65 | C, 69.34; H, 5.08; N, 18.56 | 6.55 (1H, d, J = 15.6), 7.41-7.44 (3H, m), 7.55-7.59 (2H, m), 7.82 (1H, d, J = 15.6), 8.12 (1H, brs), 8.30 (1H, dd, J = 5.7, 0.9), 8.66 (1H, d, J = 5.6), 8.89 (1H, d, J = 0.9) |
| Ia-6 | 143-144 | C14H12N2O | C, 74.98; H, 5.39; N, 12.49 | C, 74.81; H, 5.33; N, 12.72 | 6.56 (1H, d, J = 15.6), 7.07 (1H, dd, J = 7.2, 4.8), 7.38-7.42 (3H, m), 7.54-7.57 (2H, m), 7.76 (1H, ddd, J = 8.4, 7.2, 1.8), 7.79 (1H, d, J = 15.6), 8.30 (1H, m), 8.37 (1H, d, J = 8.4), 8.40 (1H, brs) |
| Ia-7 | 179-180.5 | C14H12N2O | C, 74.98; H, 5.09; N, 12.49 | C, 74.87; H, 5.54; N, 12.37 | 6.60 (1H, d, J = 15.3), 7.29 (1H, dd, J = 8.1, 4.5), 7.38-7.40 (3H, m), 7.51-7.55 (2H, m), 7.79 (1H, d, J = 15.6), 7.83 (1H, brs), 8.32 (1H, dd, J = 8.1, 1.8), 8.37 (1H, d, J = 4.5), 8.64 (1H, d, J = 1.8) |
| Ia-9 | 177-178 | C17H13N3O | C, 74.17; H, 4.76; N, 15.26 | C, 72.51; H, 4.57; N, 14.18 | *1) 6.63 (1H, d, J = 15.4), 6.81 (1H, d, J = 15.4), 7.33-7.96 (8H, m), 8.12 (1H, m), 8.39 (1H, br, s), 9.99 (1H, s) |
| Ia-10 | 115-116 | C16H16N2O | C, 76.16; H, 6.39; N, 11.10 | C, 76.35; H, 6.35; N, 11.16 | 2.35 (3H, s), 2.42 (3H, s), 6.51 (1H, d, J = 15.6), 6.76 (1H, s), 7.38-7.42 (3H, m), 7.52-7.56 (2H, m), 7.75 (1H, d, J = 15.6), 8.00 (1H, s), 8.14 (1H, brs) |

*1) NMR solvent CDCl3 + CD3OD
*2) NMR solvent DMSO-d6
*3) commercially available

TABLE 15

| Ia-16 | 136-138 | C15H14N2O | C, 75.61; H, 5.92; N, 11.76 | C, 75.69; H, 5.87; N, 11.71 | 2.38 (s, 3H), 6.52 (d, 1H, J = 15.6), 7.03-7.08 (m, 1H), 7.20 (d, 2H, J = 8.1), 7.44 (d, 2H, J = 8.1), 7.71-7.77 (m, 1H), 7.76 (d, 1H, J = 15.6), 8.29-8.31 (m, 1H), 8.37 (h, 1H, J = 8.4), 8.45 (br, 1H) |
|---|---|---|---|---|---|
| Ia-17 | 117.5-119 | C15H14N2O | C, 75.61; H, 5.92; N, 11.76 | C, 75.32; H, 5.84; N, 11.77 | 2.38 (s, 3H), 6.56 (d, 1H, J = 15.6), 7.04-7.09 (m, 1H), 7.19-7.22 (m, 1H), 7.22-7.35 (m, 3H), 7.72-7.77 (m, 1H), 7.76 (dm 1H, J = 15.6), 8.30-8.33 (m, 1H), 8.38 (d, 1H, J = 8.1), 8.57 (br, 1H) |
| Ia-18 | 145-146 | C15H14N2O | C, 75.61; H, 5.92; N, 11.76 | C, 75.57; H, 5.84; N, 11.72 | 2.46 (s, 3H), 6.48 (d, 1H, J = 15.3), 7.04-7.09 (m, 1H), 7.19-7.29 (m, 3H), 7.53-7.56 (m, 1H), 7.72-7.78 (m, 1H), 8.09 (d, 1H, J = 15.3), 8.30-8.32 (m, 1H), 8.38 (d, 1H, J = 8.4), 8.56 (br, 1H) |
| Ia-23 | | C16H16N2O | C, 76.16; H, 6.39; N, 11.10 | | *1) 2.29 (6H, s), 6.53 (1H, d, J = 15.3), 7.04-7.08 (1H, m), 7.15 (1H, m, J = 7.8), 7.26-7.30 (2H, m), 7.74 (1H, d, J = 15.3), 7.72-7.78 (1H, m), 8.31-8.33 (1H, m), 8.39 (1H, d, J = 8.4). 8.71 (1H, br) |
| Ia-27 | 186-188 | C14H13N3O | C, 70.28; H, 5.48; N, 17.56 | | 2.48 (3H, s), 6.61 (1H, d, J = 15.6), 6.94 (1H, d, J = 7.5), 7.26-7.37 (1H, m), 7.62-7.67 (1H, m), 7.77 (1H, d, J = 15.6), 7.81-7.85 (1H, m), 8.14 (1H, d, J = 8.4), 8.31 (1H, br), 8.62-8.64 (1H, m), 8.79 (1H, d, J = 1.5) |
| Ia-29 | 142-143.5 | C16H16N2O3 | C, 67.59; H, 5.67; N, 9.85 | C, 67.52; H, 5.63; N, 9.77 | *1) 3.85 (3H, s), 3.88 (3H, s), 6.47-6.54 (2H, m), 6.63 (1H, d, J = 15.6), 7.01-7.05 (1H, m), 7.44 (1H, d, J = 8.7), 7.70-7.76 (1H, m), 7.93 (1H, d, J = 15.6), 8.29-8.31 (2H, m), 8.37 (1H, d, J = 8.7) |

TABLE 15-continued

| | | | | | |
|---|---|---|---|---|---|
| Ia-30 | 199-201 | C15H11N2O | C, 61.15; H, 3.79; N, 9.59; F, 19.50 | C, 61.67; H, 3.80; N, 9.61; F, 19.37 | 6.65 (1H, d, J = 15.6), 7.06-7.13 (1H, m), 7.65 (4H, t, J = 9.6 ), 7.72-7.81 (1H, m), 7.81 (1H, d, J = 15.6), 8.29-8.35 (1H, m), 8.37 (1H, d, J = 8.1), 8.65 (1H, br) |
| Ia-37 | 189.5-191.5 | C13H10N3OCl | C, 60.12; H, 3.88; N, 16.18; Cl, 13.65 | C, 60.33; H, 3.80; N, 16.27; Cl, 13.6 | *1) 6.62 (1H, d, J = 15.6), 7.08-7.12 (1H, m), 7.28-7.32 (1H, m), 7.75-7.80 (1H, m), 7.89-7.92 (1H, m), 8.08 (1H, d, J = 15.6), 8.31-8.43 (3H, m), 8.74 (1H, br) |

TABLE 16

| | | | | | |
|---|---|---|---|---|---|
| Ia-38 | 200.5-202.5 | C14H11N2OCl | C, 65.00; H, 4.29; N, 10.83; Cl, 13.70 | C, 65.02; H, 4.20; N, 10.93; Cl, 13.70 | *1) 6.57 (1H, d, J = 15.5), 7.02-7.12 (1H, m), 7.33-7.42 (3H, m), 7.51 (1H, m), 7.72 (1H, d, J = 15.5), 7.74-7.79 (1H, m), 8.32-8.38 (2H, m), 8.68 (1H, br) |
| Ia-39 | 177-178.5 | C14H11N2OCl | C, 65.00; H, 4.29; N, 10.83; Cl, 13.70 | C, 65.01; H, 4.32; N, 10.93; Cl, 13.65 | *1) 6.54 (1H, d, J = 15.5), 7.06-7.10 (1H, m), 7.37 (2H, d, J = 8.4), 7.47 (2H, d, J = 8.4), 7.74 (1H, d, J = 15.5), 7.73-7.79 (1H, m), 8.30-8.32 (1H, m), 8.36 (1H, d, J = 8.4), 8.58 (1H, br) |
| Ia-40 | 131-132 | C14H10N2OCl2 | C, 57.36; H, 3.44; N, 9.56; Cl, 24.19 | C, 57.33; H, 3.35; N, 9.64; Cl, 24.08 | 6.55 (1H, d, J = 15.6), 7.05-7.13 (1H, m), 7.36 (1H, dd, J = 2.1, 8.4), 7.48 (1H, d, J = 8.1), 7.62 (1H, d, J = 2.4), 7.68 (1H, d, J = 15.6), 7.72-7.81 (1H, m), 8.28-8.38 (2H, m), 8.46 (1H, br) |
| Ia-42 | 205-206 | C13H10N3OCl | C, 60.12; H, 3.88; N, 16.88; Cl, 13.65 | C, 60.28; H, 3.88; N, 16.26; Cl, 13.57 | *2) 7.15 (d, 1H, J = 15.9), 7.13-7.16 (m, 1H), 7.63 (d, 1H, J = 8.4), 7.68 (d, 1H, J = 15.9), 7.80-7.86 (m, 1H), 8.07 (dd, 1H, J = 2.4 and J = 8.4), 8.24 (d, 1H, J = 7.8), 8.35-8.37 (m, 1H), 8.66 (d, 1H, J = 2.4), 10.75 (s, 1H) |
| Ia-44 | 147-149 | C14H11N2OF | C, 69.41; H, 4.58; N, 11.56; F, 7.84 | C, 69, 60; H, 4.56; N, 11.60; F, 7.90 | 6.49 (d, 1H, J = 15.5), 7.05-7.12 (m, 3H), 7.50-7.55 (2H, m), 7.73-7.78 (m, 2H), 8.30-8.33 (1H, m), 8.36 (d, 1H, J = 8.1), 8.58 (br, 1H) |
| Ia-45 | 171-172 | C14H11N2OF | C, 69.41; H, 4.58; N, 11.56; F, 7.84 | C, 69.53; H, 4.55; N, 11.65; F, 7.89 | 6.68 (d, 1H, J = 15.4), 7.05-7.42 (m, 5H), 7.75 (d, 1H, J = 15.4), 7.72-7.81 (m, 1H), 8.31-8.40 (m, 2H), 8.82 (br, 1H) |
| Ia-48 | 154-154.5 | C14H11N2OF | C, 69.41; H, 4.58; N, 11.56; F, 7.84 | C, 69.58; H, 4.52; N, 11.61; F, 7.97 | 6.74 (d, 1H, J = 16.2), 7.05-7.21 (m, 3H), 7.30-7.41 (m, 1H), 7.47-7.55 (m, 1H), 7.72-7.81 (m, 1H), 7.87 (d, 1H, J = 16.2), 8.32-8.35 (m, 1H), 8.39 (d, 1H, J = 8.4), 8.99 (br, 1H) |
| Ia-46 | 181-182 | C13H10N3OF | C, 64.29; H, 4.14; N, 17.28; F, 7.81 | C, 64.48; H, 4.20; N, 17.18; F, 7.63 | 6.59 (1H, d, J = 15.6), 6.99 (1H, dd, J = 3.0 and 8.4), 7.08-7.13 (1H, m), 7.75-7.80 (2H, m), 7.92-7.99 (1H, m), 8.31-8.38 (2H, m), 8.39 (1H, d, J = 2.4), 8.79 (1H, br) |
| Ia-53 | 158-159.5 | C18H20N2O3 | C, 69.21; H, 6.45; N, 8.97 | C, 69.29; H, 6.37; N, 8.99 | *1) 1.48 (3H, t, J = 6.9), 1.48 (3H, t, J = 6.9), 4.12 (2H, q, J = 6.9), 4.14 (2H, q, J = 6.9), 6.41 (1H, d, J = 15.5), 6.87 (1H, d, J = 8.4), 7.03-7.12 (3H, m); 7.70 (1H, d, J = 15.5), 7.71-7.77 (1H, m), 8.29-8.32 (1H, m), 8.37 (1H, d, J = 8.4), 8.43 (1H, br) |

TABLE 17

| | | | | | |
|---|---|---|---|---|---|
| Ia-54 | 148.5-149.5 | C16H16N2O3 | C, 67.59; H, 5.67; N, 9.85 | C, 67.70; H, 5.59; N, 9.78 | *1) 3.87 (3H, s), 3.89 (3H, s), 6.68 (1H, d, J = 15.8), 6.93-6.97 (1H, m), 7.04-7.16 (3H, m), 7.72-7.78 (1H, m), 8.05 (1H, d, J = 15.8), 8.30-8.33 (1H, m), 8.38 (1H, d, J = 8.4), 8.58 (1H, br) |
| Ia-55 | 157-158.5 | C16H16N2O3 | C, 67.59; H, 5.67; N, 9.85 | C, 67.73; H, 5.55; N, 9.90 | 3.92 (s, 6H), 6.45 (d, 1H, J = 15.5), 6.88 (d, 1H, J = 8.1), 7.03-7.08 (m, 2H), 7.12-7.15 (m, 1H), 7.71-7.77 (m, 1H), 7.72 (d, 1H, J = 15.5), 8.30-8.32 (m, 1H), 8.37 (d, 1H, J = 8.7), 8.55 (br, 1H) |
| Ia-59 | 181-182 | C16H16N2O3 | C, 67.59; H, 5.67; N, 9.85 | C, 67.64; H, 5.44; N, 9.88 | *1) 3.80 (3H, s), 3.84 (3H, s), 6.72 (1H, d, J = 15.5), 6.85-6.94 (2H, m), 7.04-7.08 (2H, m), 7.17-7.77 (1H, m), 7.98 (1H, d, J = 15.5), 8.30-8.33 (1H, m), 8.38 (1H, d, J = 8.4), 8.59 (1H, br) |
| Ia-60 | 171-173 | C16H16N2O3 | C, 67.59; H, 5.67; N, 9.85 | C, 67.57; H, 5.57; N, 9.90 | *1) 3.82 (6H, s), 6.50-6.51 (1H, m), 6.54 (1H, d, J = 15.9), 6.68 (2H, d, J = 2.1), 7.05-7.09 (1H, m), 7.70 (1H, d, J = 15.9), 7.72-7.78 (1H, m), 8.31-8.33 (1H, m), 8.37 (1H, d, J = 8.7), 8.62 (1H, br) |
| Ia-61 | 141-143 | C17H17NO3 | C, 72.07; H, 6.05; N, 4.94 | C, 71.85; H, 6.03; N, 5.01 | 3.86 (3H, s), 3.88 (3H, s), 6.65 (1H, d, J = 15.6), 6.91-7.39 (6H, m), 7.47 (1H, brs), 7.63 (1H, brd, J = 8.0) |
| Ia-62 | amorphous | C17H17NO3 | C, 72.07; H, 6.05; N, 4.94 | C, 72.01; H, 6.18; N, 5.11 | 3.93 (3H, s), 3.94 (3H, s), 6.39 (1H, d, J = 15.9), 6.90 (1H, d, J = 8.7), 7.08-7.39 (8H, m), 7.80 (1H, d, J = 15.9) |
| Ia-63 | 170.5-172 | C17H17NO3 | C, 72.07; H, 6.05; N, 4.94 | C, 72.11; H, 6.08; N, 5.06 | 3.80 (3H, s), 3.86 (3H, s), 6.68 (1H, d, J = 15.4), 6.83-7.39 (6H, m), 7.40 (1H, brs), 7.62 (2H, brd, J = 8.0) |
| Ia-64 | 141-142 | C18H19NO4 | C, 68.99; H, 6.11; N, 4.47 | C, 69.09; H, 6.02; N, 4.43 | 3.80 (3H, s), 3.85 (3H, s), 3.87 (3H, s), 6.64 (1H, d, J = 15.6), 6.85-7.13 (5H, m), 7.47 (1H, brs), 7.55 (2H, brd) |
| Ia-65 | 168.5-169.5 | C18H19NO4 | C, 68.99; H, 6.11; N, 4.47 | C, 69.13; H, 6:08; H, 4.48 | 3.81 (3H, s), 3.91 (6H, s), 6.41 (1H, d, J = 15.4), 6.85-7.15 (5H, m), 7.52 (2H, brd, J = 8), 7.68 (1H, d, J = 15.4) |

TABLE 17-continued

| ID | mp | Formula | Calc | Found | NMR |
|---|---|---|---|---|---|
| Ia-69 | 129.5-131.5 | C17H18N2O4 | C, 64.94; H, 5.77; N, 8.91 | | 3.89 (9H, s), 6.50 (1H, d, J-5.5), 6.76 (2H, s), 7.05-7.09 (1H, m), 7.70 (1H, d, J = 15.5), 7.73-7.79 (1H, m), 8.32-8.34 (1H, m), 8.38 (1H, d, J = 8.1), 8.85 (1H, br) |

TABLE 18

| ID | mp | Formula | Calc | Found | NMR |
|---|---|---|---|---|---|
| Ia-77 | 179-180 | C16H16N2O3 | C, 67.59; H, 5.67; N, 9.85 | C, 67.46; H, 5.66; N, 9.80 | *1) 3.87 (6H, s), 6.57 (2H, d, J = 8.7), 7.01-7.05 (1H, m), 7.08 (1H, d, J = 15.9), 7.25-7.30 (1H, m), 7.70-7.76 (1H, m), 8.23 (1H, d, J = 15.9), 8.29-8.32 (1H, m), 8.41 (1H, d, J = 8.4), 8.56 (1H, br) |
| Ia-95 | 180-182 | C13H12N4O | C, 64.99; H, 5.03; N, 23.32 | C, 65.09; H, 5.05; N, 23.25 | *2) 5.80 (br 2H), 6.20-6.23 (m, 1H), 7.15 (d, 1H, J = 15.9), 7.38-7.40 (m, 2H), 7.46-7.50 (m, 1H), 7.61 (d, 1H, d = 15.9), 7.97-7.99 (m, 1H), 8.57-8.59 (m, 1H), 8.79 (d, 1H, J = 1.8), 10.12 (s, 1H) |
| Ia-97 | 249-251 | C14H14N4O | C, 66.13; H, 5.55; N, 22.03 | | *2) 2.82 (3H, d, J = 4.8), 6.53 (1H, d, J = 9.0), 6.75 (1H, d, J = 15.6), 7.07-7.11 (2H, m), 7.50 (1H, d, J = 15.6), 7.61 (1H, dd, J = 2.3 and 9.0), 7.76-7.81 (1H, m), 8.21-8.25 (2H, m), 8.31-8.34 (1H, m), 10.49 (1H, s) |
| Ia-104 | 157-158 | C12H10N2O2 | C, 67.28; H, 4.71; N, 13.08 | C, 67.58; H, 4.77; N, 13.10 | 6.47 (1H, d, J = 15.6), 6.48 (1H, dd, J = 3.3, 1.8), 6.62 (1H, d, J = 3.3), 7.06 (1H, ddd, J = 7.2, 4.8, 0.9), 7.48 (1H, d, J = 1.8), 7.55 (1H, d, J = 15.6), 7.73 (1H, ddd, J = 7.2, 1.8), 8.30 (1H, m), 8.35 (1H, d, J = 8.1), 8.48 (1H, brs) |
| Ia-105 | 140-141 | C12H10N2OS | C, 62.59; H, 4.38; N, 12.16; S, 13.92 | C, 62.78; H, 4.42; N, 12.07; S, 13.99 | 6.40 (1H, d, J = 15.3), 7.06 (1H, dd, J = 5.1, 3.6), 7.08 (1H, ddd, J = 8.0, 4.8, 0.9), 7.26 (1H, d, J = 3.6), 7.36 (1H, d, J = 5.1), 7.75 (1H, ddd, J = 8.7, 8.0, 2.1), 7.90 (1H, d, J = 15.3), 8.33 (1H, m), 8.38 (1H, d, J = 8.7), 9.02 (1H, brs) |
| Ia-112 | 208-209 | C13H11N3O | C, 69.32; H, 4.92; N, 18.66 | C, 69.48; H, 4.87; N, 18.73 | *1) 6.85 (1H, d, J = 15.6), 7.10 (1H, ddd, J = 6.3, 5.1, 1.2), 7.40 (1H, dd, J = 8.1, 5.1), 7.75 (1H, d, J = 15.6), 7.78 (1H, ddd, J = 8.4, 6.3, 2.1), 7.94 (1H, ddd, J = 8.1, 2.4, 1.2), 8.29 (1H, m), 8.35 (1H, d, J = 8.4), 8.56 (1H, dd, J = 5.1, 1.2), 8.77 (1H, d, J = 2.4) |
| Ia-113 | 178-179 | C13H11N3O | C, 69.32; H, 4.92; N, 18.6 | C, 69.32; H, 4.97; N, 18.71 | 7.06 (1H, ddd, J = 8.4, 5.1, 0.9), 7.16 (1H, d, J = 15.3), 7.28 (1H, ddd, J = 7.5, 4.8, 1.2), 7.41 (1H, d, J = 7.5), 7.73 (1H, dt, J = 7.5, 1.8), 7.76 (1H, td, J = 8.4, 1.8), 7.77 (1H, d, J = 15.3), 8.33 (1H, m), 8.36 (1H, d, J = 8.4), 8.65 (1H, m) |

TABLE 19

| ID | mp | Formula | Calc | Found | NMR |
|---|---|---|---|---|---|
| Ia-118 | 150.5-152 | C12H10NO2 | C, 67.28; H, 4.70; N, 13.08 | C, 67.23; H, 4.73; N, 13.08 | 6.30 (d, 1H, J = 15.6), 6.56-6.57 (m, 1H), 7.05-7.09 (m, 1H), 7.43-7.45 (m, 1H), 7.66-7.78 (m, 3H), 8.30-8.33 (m, 1H), 8.37 (1H, J = 7.2), 8.77 (br, 1H) |
| Ia-119 | 1555.5-156.5 | C12H10N2OS | C, 62.59; H, 4.38; N, 12.16; S, 13.92 | C, 62.64; H, 4.41; N, 12.10; S, 13.94 | 6.40 (1H, d, J = 15.3), 7.06 (1H, ddd, J = 7.5, 4.8, 1.2), 7.27 (1H, m), 7.35 (1H, m), 7.51 (1H, dd, J = 2.7, 0.9), 7.75 (1H, ddd, J = 8.4, 7.5, 1.8), 7.77 (1H, d, J = 15.3), 8.30 (1H, m), 8.36 (1H, d, J = 8.4), 8.80 (1H, brs) |
| Ia-120 | 179-181 | C13H11N3O | C, 69.32; H, 4.92; N, 18.65 | C, 69.35; H, 4.88; N, 18.67 | 6.76 (d, 1H, J = 15.6), 7.09-7.13 (m, 1H), 7.36-7.38 (m, 2H), 7.72 (d, 1H, J = 15.6), 7.75-7.81 (m, 1H), 8.32-8.38 (m, 2H), 8.66-8.68 (m, 2H), 8.90 (br, 1H) |
| Ia-131 | 212-215 | C17H14N2O2 | C, 73.37; H, 5.07; N, 10.07 | C, 73.58; H, 4.83; N, 10.14 | 4.98 (2H, s), 5.87 (1H, d, J = 15.3), 6.84 (1H, d, J = 8.1), 6.87-6.97 (1H, m), 7.00-7.23 (3H, m), 7.48 (1H, d, J = 15.3), 7.70-7.79 (1H, m), 8.26-8.36 (2H, m), 8.39 (1H, br) |
| Ia-144 | 140-141 | C16H15NO2 | C, 75.87; H, 5.97; N, 5.53 | C, 75.88; H, 5.90; N, 5.63 | 3.84 (3H, s), 6.43 (1H, d, J = 15.6), 6.94 (2H, d, J = 8.8), 7.12 (1H, m), 7.34 (2H, m), 7.45 (1H, brs), 7.47 (2H, d, J = 8.8), 7.61 (2H, brd, J = 8), 6.71 (1H, d, J = 15.6) |
| Ia-145 | 104-105 | C16H15NO2 | C, 75.87; H, 5.97; N, 5.53 | C, 75.83; H, 6.08; N, 5.61 | 3.84 (3H, s), 6.93 (1H, m), 7.06 (1H, m), 7.14 (2H, m), 7.28-7.38 (4H, m), 7.62 (2H, brd), 7.73 (1H, d, J = 15.6) |
| Ia-146 | 164-166 | C16H15NO2 | C, 75.87; H, 5.97; N, 5.53 | C, 76.10; H, 5.93; N, 5.53 | 3.89 (3H, s), 6.70 (1H, d, J = 15.6), 6.90-6.98 (2H, m), 7.08-7.15 (1H, m), 7.30-7.50 (5H, m), 7.63 (2H, brd, J = 8.0), 8.00 (1H, d, J = 15.6) |
| Ia-150 | 207-209 | C14H13N3O2 | C, 65.87; H, 5.17; N, 16.46 | C, 65.92; H, 5.27; N, 16.42 | 2) 3.91 (3H, s), 6.94 (1H, d, J = 8.7), 7.48 (1H, d, J = 15.8), 7.10-7.14 (1H, m), 7.64 (1H, d, J = 15.8), 7.78-7.84 (1H, m), 7.94 (1H, dd, J = 2.4 and 8.7), 8.24 (1H, d, J = 8.4), 8.33-8.36 (1H, m), 8.42 (1H, d, J = 2.4), 10.65 (1H, a) |
| Ia-151 | 185-186 | C17H17NO30.2H2O | C, 72.07; H, 6.05; N, 4.94 | C, 71.16; H, 6.11; N, 4.88 | 3.80 (3H, s), 3.84 (3H, s), 6.40 (1H, d, J = 15.6), 6.86-6.92 (4H, m), 6.45-7.53 (4H, m), 7.69 (1H, d, J = 15.6) |
| Ia-152 | 119.5-121 | C15H14N2O2 | C, 70.85; H, 5.55; N, 11.02 | C, 70.91; H, 5.46; N, 11.01 | 3.83 (3H, s), 6.57 (1H, d, J = 15.4), 6.91-6.96 (m, 1H), 7.04-7.15 (m, 3H), 7.27-7.35 (m, 1H), 7.72-7.79 (m, 2H), 8.31-8.33 (m, 1H), 8.34 (d, 1H, J = 8.4), 8.75 (br, 1H) |

TABLE 20

| ID | mp | Formula | Calc | Found | NMR |
|---|---|---|---|---|---|
| Ia-153 | 130-131 | C15H14N2O2 | C, 70.85; H, 5.55; N, 11.02 | C, 70.89; H, 5.26; N, 11.02 | 3.85 (3H, s), 6.43 (1H, d, J = 15.3), 6.92 (2H, d, J = 8.7), 7.05 (1H, ddd, J = 7.2, 5.1, 1.2), 7.49 (2H, d, J = 8.7), 7.74 (1H, d, |

TABLE 20-continued

| | | | | | |
|---|---|---|---|---|---|
| | | | | | J = 15.3), 7.74 (1H, ddd, J = 8.4, 7.2, 2.1), 8.30 (1H, m), 8.36 (1H, d, J = 8.4), 8.36 (1H, brs) |
| Ia-156 | 137-138.5 | C15H14N2O2 | C, 70.85; H, 5.55; N, 11.02 | C, 70.77; H, 5.44; N, 11.06 | *1) 3.89 (3H, s), 6.74 (1H, d, J = 15.6), 6.92-7.07 (3H, m), 7.33-7.38 (1H, m), 7.49-7.52 (1H, m), 7.71-7.77 (1H, m), 8.02 (1H, d, J = 15.6), 8.30-8.40 (1H, m), 8.39 (1H, d, J = 8.2), 8.55 (1H, br) |
| Ia-161 | 199-200.5 | C15H12N2O3 | C, 67.16; H, 4.51; N, 10.44 | C, 67.27; H, 4.46; N, 10.45 | 6.02 (s, 2H), 6.39 (d, 1H, J = 15.5), 6.82 (d, 1H, J = 8.4), 7.01-1.08 (m, 3H), 7.69 (d, 1H, J = 15.5), 7.71-7.77 (m, 1H), 8.30-8.38 (m, 2H), 8.53 (br, 1H) |
| Ia-162 | 177-178 | C17H15NO4 | C, 68.68; H, 5.09; N, 4.71 | C, 68.54; H, 5, 06; N, 4.71 | 3.80 (3H, s), 6.00 (2H, s), 6.35 (1H, d, J = 15.6), 6.80-7.02 (5H, m), 7.25 (1H, brs), 7.52 (2H, brd, J = 7.8), 7.65 (1H, d, J = 15.6) |
| Ia-177 | 272.5-274 (dec) | C14H10N4OS | C, 59.56; H, 3.57; N, 19.84; S, 11.36 | C, 59.26; H, 3.56; N, 19.65; S, 11.32 | *2) 7.13-7.17 (1H, m), 7.28 (1H, d, J = 15.8), 7.81-7.87 (1H, m), 7.89 (1H, d, J = 15.8), 7.94-7.97 (1H, m), 8.19 (1H, d, J = 9.6), 8.27 (1H, d, J = 8.4), 8.36-8.39 (2H, m), 10.79 (1H, s) |
| Ia-203 | 295-297 (dec) | C10H8N4OS | C, 51.71; H, 3.47; N, 24.12; S, 13.81 | C, 51.69; H, 3.47; N, 24.06; S, 13.68 | *2) 7.05 (1H, d, J = 15.9), 7.51 (1H, dd, J = 4.8, 7.8), 7.83 (1H, d, J = 15.9), 8.07 (1H, d, J = 7.8), 8.63 (1H, d, J = 4.8), 8.85 (1H, s), 9.21 (1H, s), 12.88 (1H, br) |
| Ia-204 | 252-254 | C11H9N3OS | C, 57.13; H, 3.92; N, 18.17; S, 13.86 | C, 57.10; H, 3.92; N, 18.20; S, 13.76 | *2) 7.02 (1H, d, J = 15.9), 7.27 (1H, d, J = 3.6), 7.50 (1H, dd, J = 4.8, 8.1), 7.53 (1H, d, J = 3.6), 7.77 (1H, d, J = 15.9), 8.01-8.08 (1H, m), 8.61 (1H, dd, J = 1.8, 4.8), 8.83 (1H, d, J = 1.8), 12.42 (1H, br) |
| Ib-1 | 162-164 | C13H11NO | C, 79.16; H, 5.62; N, 7.10 | C, 78.98; H, 5.62; N, 7.13 | 7.12-7.20 (1H, m), 7.34-7.67 (7H, m), 7.85-7.90 (3H, m) |
| Ib-2 | 69-70 | C15H15NO2 | C, 74.67; H, 6.27; N, 5.80 | C, 74.60; H, 6.18; N, 5.93 | 1.64 (t, 3H, J = 7.1), 4.29 (q, 2H, J = 7.1), 7.01 (d, 1H, J = 8.1), 7.10-7.15 (m, 2H), 7.34-7.39 (m, 2 H), 7.44-7.50 (m, 1H), 7.67-7.70 (m, 2H), 8.31 (dd, 1H, J = 2.0 and 7.7), 10.13 (1H, br) |

TABLE 21

| | | | | | |
|---|---|---|---|---|---|
| Ib-3 | 161.5-162.5 | C15H11NO2 | C, 75.94; H, 4.67; N, 5.90 | C, 76.04; H, 4.59; N, 6.04 | 7.18 (1H, t, J = 7.5), 7.33-7.74 (8H, m), 8.34 (1H, brs) |
| Ib-4 | 142.5-143.5 | C15H15NO | C, 79.97; H, 6.71; N, 6.22 | C, 79.73; H, 6.72; N, 6.25 | 2.34 (3H, s), 2.50 (3H, s), 7.17 (2H, d, J = 8.4), 7.25-7.27 (2H, m), 7.33-7.39 (1H, m), 7.41 (1H, br), 7.46-7.75 (3H, m) |
| Ib-5 | oil | C15H15NO2 | C, 74.67; H, 6.27; N, 5.80 | C, 74.32; H, 6.26; H, 5.77 | 2.34 (3H, s), 4.05 (3H, s), 7.03 (1H, d, J = 8.4), 7.11-7.16 (1H, m), 7.16 (2H, d, J = 8.1), 7.46-7.52 (1H, m), 7.56 (2H, d, J = 8.1), 8.29 (1H, dd, J = 1.8 and 7.8), 9.73 (1H, br) |
| Ib-6 | 132-133 | C14H12ClNO | C, 68.44; H, 4.92; N, 5.70; Cl, 14.43 | C, 68.25; N, 4.96; N, 5.78; Cl, 14.40 | 2.35 (3H, s), 7.18 (2H, d, J = 8.4), 7.36-7.47 (3H, m), 7.53 (2H, d, J = 8.4), 7.74-7.79 (1H, m), 7.82 (1H, br) |
| Ib-7 | 107-109 | C15H15NO | C, 79.97; H, 6.71; N, 6.22 | C, 79.71; H, 6.72; N, 6.26 | 2.34 (3H, s), 2.43 (3H, s), 7.17 (2H, d, J = 8.4), 7.35-7.37 (2H, m), 7.52 (2H, d, J = 8.4), 7.62-7.65 (1H, m), 7.68 (1H, s), 7.74 (1H, br) |
| Ib-8 | 127-129 | C15H15NO2 | C, 74.67; H, 6.27; N, 5.80 | C, 74.59; H, 6.31; N, 5.86 | 2.34 (3H, s), 3.86 (3H, s), 7.05-7.10 (1H, m), 7.17 (2H, d, J = 8.4), 7.36-7.38 (2H, m), 7.43-7.44 (1H, m), 7.51 (2H, d, J = 8.4), 7.77 (1H, br) |
| Ib-9 | 122-124.5 | C14H12ClNO | C, 68.44; H, 4.92; N, 5.70; Cl, 14.43 | C, 68.42; H, 4.95; N, 5.77; Cl, 14.44 | 2.35 (3H, s), 7.19 (2H, d, J = 8.1), 7.40-7.45 (1H, m), 7.50-7.54 (3H, m), 7.72-7.75 (2H, m), 7.85-7.86 (1H, m) |
| Ib-10 | 198-199.5 | C18H15NO | C, 89.73; H, 5.79; N, 5.36 | C, 89.82; H, 5.70; N, 5.46 | *2) 2.30 (3H, s), 7.18 (2H, d, J = 8.7), 7.58-7.63 (3H, m), 7.68-7.75 (3H, m), 8.00-8.08 (2H, m), 8.16-8.19 (1H, m), 10.48 (1H, s) |
| Ib-11 | *3 | | | | |
| Ib-12 | 173-175 | C15H13NO2 | C, 75.30; H, 5.48; N, 5.85 | | 2.35 (s, 3H), 7.18-7.20 (m, 3H), 7.53 (d, 2H, J = 8.4), 7.86 (br, 1H), 7.96-8.03 (m, 3H), 10.10 (s, 1H) |
| Ib-13 | 202-204 | C16H15NO3 | C, 74.67; H, 6.29; N, 5.80 | C, 74.59; H, 6.31; N, 5.86 | *2) 2.29 (s, 3H), 3.90 (s, 3H), 7.17 (d, 2H, J = 8.6), 7.66 (d, 2H, J = 8.6), 8.07-8.08 (m, 4H), 10.35 (s, 1H) |
| Ib-14 | 312-314 | C15H13NO3 | C, 70.58; H, 5.13; N, 5.49 | C, 10.81; H, 5.22; N, 5.70 | 2.28 (3H, s), 7.16 (d, 2H, J = 8.4), 7.70 (d, 2H, J = 8.4), 8.05-8.06 (m, 4H), 10.45 (s, 1H) |

TABLE 22

| | | | | | |
|---|---|---|---|---|---|
| Ib-15 | 206.5-208.5 | C19H19NO3 | C, 73.77; H, 6.19; N, 4.53 | C, 73.94; H, 6.09; N, 4.82 | *2) 1.28 (t, 3H, J = 7.1), 2.28 (s, 3H), 4.22 (q, 2H, J = 7.1), 6.78 (d, 1H, J = 16.2), 7.16 (d, 2H, J = 8.4), 7.66 (d, 2H, J = 8.4), 7.71 (d, 1H, J = 16.2), 7.88 (d, 2H, J = 8.4), 7.98 (d, 2H, J = 8.4). 10.23 (s, 1H) |
| Ib-16 | 300-302 (dec) | C17H15NO3 | C, 72.58; H, 5.37; 5.98 | C, 72.59; H, 5.43; N, 5.35 | *2) 2.28 (3H, s), 6.67 (1H, d, J = 16.2), 7.16 (2H, d, J = 8.7), 7.66 (1H, d, J = 16.2), 7.66 (2H, d, J = 8.7), 7.85 (2H, d, J = 8.4), 7.98 (2H, d, J = 8.4), 10.22 (1H, s) |
| Ib-17 | 215-217 | C14H12NOCl | C, 68.43; H, 4.92; N, 5.70 | C, 68.53; H, 5.01; N, 5.84 | *2) 2.28 (3H, s), 7.16 (2H, d, J = 8.9), 7.60 (2H, d, J = 8.9), 7.65 (2H, d, J = 8.9), 7.98 (2H, d, J = 8.9) |
| Ib-18 | 155-157 | C15H15NO2 | C, 74.67; H, 6.72; N, 5.80 | C, 74.74; H, 6.19; N, 5.88 | 2.34 (s, 3H), 3.87 (s, 3H), 6.97 (d, 2H, J = 8.8), 7.16 (d, 2H, J = 8.2), 7.51 (d, 2H, J = 8.2), 7.70 (br, 1H), 7.83 (d, 2H, J = 8.8) |
| Ib-19 | 174-175 | C16H17NO2 | C, 75.27; H, 6.71; N, 5.49 | C, 75.32; H, 6.63; N, 5.56 | 1.45 (3H, t, J = 7.2), 2.33 (3H, s), 4.09 (2H, q, J = 7.2), 6.95 (2H, d, J = 9.0), 7.16 (2H, d, J = 8.6), 7.50 (2H, d, J = 8.6), 7.69 (1H, br), 7.82 (2H, d, J = 9.0) |

TABLE 22-continued

| | | | | | |
|---|---|---|---|---|---|
| Ib-20 | 192-194 | C18H15NO | C, 82.73; H, 5.79; N, 5.36 | C, 82.72; H, 5.82; N, 5.45 | *2) 3.33 (3H, s), 7.18 (2H, d, J = 8.4), 7.12-7.65 (2H, m), 7.71 (2H, d, J = 8.4), 8.00-8.10 (4H, m), 8.57 (1H, s), 10.35 (1H, s) |
| Ib-21 | *3 | | | | |
| Ib-22 | 150-155 | C19H23NO | C, 81.10; H, 8.24; N, 4.98 | C, 80.85; H, 8.31; N, 5.19 | 1.25 (3H, d, J = 6.6), 1.28 (3H, d, J = 6.6), 2.81-3.07 (1H, m), 7.22 (2H, d, J = 8.9), 7.33 (2H, d, J = 8.9), 7.55 (2H, d, J = 8.9), 7.79 (2H, d, J = 8.9) |
| Ib-23 | *3 | | | | |
| Ib-24 | 158-159 | C14H13NO2 | C, 73.99; H, 5.77; N, 6.16 | C, 74.02; H, 5.83; N, 6.25 | 3.82 (3H, s), 6.91 (2H, d, J = 9.2), 7.43-7.6 (5H, m), 7.76 (1H, brs), 7.84-7.89 (2H, m) |
| Ib-25 | *3 | | | | |
| Ib-26 | 215-216 | C14H12NOCl | C, 68.43; H, 4.92; N, 5.70 | C, 68.52; H, 4.89; N, 5.86 | *2) 2.39 (3H, s), 7.34 (2H, d, J = 8.6), 7.40 (2H, d, J = 9.2), 7.82 (2H, d, J = 9.2), 7.87 (2H, d, J = 8.6) |
| Ib-27 | oil | C14H13NO | | | 2.26 (3H, s), 2.28 (3H, s), 3.46 (3H, s), 6.89-7.05 (6H, m), 7.19 (2H, d, J = 8.2), |

TABLE 23

| | | | | | |
|---|---|---|---|---|---|
| Ib-28 | 213-214 | C13H9NOCl2 | C, 58.67; H, 3.41; N, 5.26 | C, 58.45; H, 3.49; N, 5.38 | *2) 7.42 (2H, d, J = 9.2), 7.62 (2H, d, J = 8.6), 7.81 (2H, d, J = 9.2), 7.98 (2H, d, J = 8.6) |
| Ib-29 | 245-247 | C20H17N1O1 | C, 83.59; H, 5.96N, 4.87 | C, 83.70; H, 5.96N, 4.87 | 2.35 (3H, s), 7.39-7.52 (3H, m), 7.55 (2H, d, J = 8.4), 7.55 (2H, d, J = 8.4), 7.57-7.66 (2H, m), 7.70 (2H, d, J = 8.4), 7.96 (2H, d, J = 8.4) |
| Ib-30 | 257-258 | C20H17N1O2 | C, 79.19; H, 5.65 N, 4.62 | C, 79.12; H, 5.57 N, 4.77 | *2) 3.75 (3H, s), 6.93 (2H, d, J = 9.2), 7.42-7.55 (3H, m), 7.70 (2H, d, J = 9.2), 7.76 (2H, m), 7.83 (2H, d, J = 8.4), 8.05 (2H, d, J = 8.4), 10.17 (1H, s) |
| Ib-31 | 256-258 (dec) | C18H1NO5 | C, 66.46; H, 4.65; N, 4.31 | C, 66.10; H, 4.75; N, 4.51 | *2) 3.77 (3H, s), 3.89 (3H, s), 6.93 (1H, s), 6.99 (2H, d, J = 8.9), 7.45 (1H, d, J = 3.0), 7.53 (1H, dd, J = 3.0, 9.2), 7.70 (2H, d, J = 8.9), 7.80 (1H, d, J = 9.2), 10.62 (1H, s) |
| Ib-35 | 162-163 | C18H14N2O | C, 78.81; H, 5.14; N, 10.21 | C, 78.66; H, 5.08; N, 10.18 | 7.09 (1H, ddd, J = 7.2, 5.1, 1.2), 7.38-7.76 (7H, m), 7.77 (1H, ddd, J = 8.4, 7.2, 2.1), 8.02 (2H, d, J = 8.1), 8.32 (1H, brd), 8.43 (1H, d, J = 8.4), 8.71 (1H, brs) |
| Ib-73 | 118-119 | C11H9N3O | C, 66.32; H, 4.55; N, 21.09 | C, 66.37; H, 4.48; S, 21.02 | 7.08 (1H, ddd, J = 7.5, 4.8, 1.2), 7.50 (1H, ddd, J = 7.8, 4.8, 1.2), 7.77 (1H, ddd, J = 8.1, 7.5, 1.8), 7.91 (1H, td, J = 7.8, 1.8), 8.30 (1H, m), 8.36 (1H, m), 8.43 (1H, d, J = 8.1)), 8.64 (1H, m) |
| Ib-77 | 138-140 | C11H9N3O | C, 66.32; H, 4.55; N, 21.09 | C, 66.49; H, 4.47; N, 20.79 | 7.11 (1H, ddd, J = 7.2, 4.8, 1.2), 7.46 (1H, ddd, J = 7.8, 4.8, 0.6), 7.79 (1H, ddd, J = 8.7, 7.2, 1.8), 8.25 (1H, ddd, J = 7.8, 2.4, 1.2), 8.30 (1H, m), 8.38 (1H, d, J = 8.7), 8.81 (1H, dd, J = 4.8, 1.2), 9.18 (1H, brd) |
| Ib-80 | 141-142 | C11H9N3O | C, 66.32; H, 4.55; N, 21.09 | C, 66.46; H, 4.47; N, 21.15 | 7.11 (1H, ddd, J = 7.5, 4.8, 0.8), 7.80 (1H, ddd, J = 8.1, 7.5, 2.1), 7.76 and 8.82 (4H, AB, J = 6.0), 8.27 (1H, m), 8.37 (1H, d, J = 8.1), 8.80 (1H, brs) |
| Ib-97 | 98-99 | C15H13N3O0.25N2O | C, 71.70; H, 5.21; N, 16.72 | C, 70.43; H, 5.32; N, 16.43 | 4.12 (3H, s), 7.08 (1H, dd, J = 7.0, 5.4), 7.13 (1H, s), 7.18 (1H, m), 7.37 (1H, m), 7.42 (1H, d, J = 7.8), 7.69 (1H, d, J = 8.1), 7.78 (1H, ddd, J = 8.4, 7.0, 1.8), 8.33 (1H, m), 8.34 (1H, d, J = 8.1) |

TABLE 24

| | | | | | |
|---|---|---|---|---|---|
| Ib-102 | 140-141 | C14H10N2O2 | C, 70.58; H, 4.23; N, 11.76 | C, 70.59; H, 4.21; N, 11.72 | 7.10 (1H, ddd, J = 7.8, 5.1, 0.6), 7.33 (1H, m), 7.47 (1H, m), 7.56 (1H, d, J = 8.4), 7.63 (1H, s), 7.71 (1H, dd, J = 8.4, 1.2), 7.77 (1H, dt, J = 7.8, 2.1), 8.36 (1H, m), 8.38 (1H, d, J = 7.8), 9.02 (1H, brs) |
| Ib-105 | 200-202 | C14H11N3O | C, 70.87; H, 4.67; N, 17.71 | C, 70.83; H, 4.64; N, 17.62 | 7.09 (1H, dd, J = 7.8, 4.8), 7.16 (1H, s), 7.16 (1H, m), 7.33 (1H, m), 7.45 (1H, d, J = 8.4), 7.67 (1H, d, J = 8.1), 7.75 (1H, ddd, J = 8.1, 7.8, 1.8), 8.36 (1H, m), 8.40 (1H, d, J = 8.1), 8.90 (1H, brs), 9.71 (1H, brs) |
| Ib-122 | 129-131 | C10H8N2OS0.1H2O | C, 58.80; H, 3.95; N, 13.72; S, 15.70 | C, 58.29; H, 4.01; N, 13.60; S, 15.56 | 7.08 (1H, dd, J = 7.5, 5.1), 7.14 (1H, dd, J = 5.1, 3.9), 7.59 (1H, dd, J = 5.1, 1.2), 7.69 (1H, dd, J = 3.9, 1.2), 7.76 (1H, ddd, J = 8.4, 7.5, 2.1), 8.30 (1H, m), 8.33 (1H, d, J = 8.4) |
| Ib-124 | 106-107 | C10H8N2OS | C, 58.80; H, 3.95; N, 13.72; S, 15.70 | C, 58.93; H, 3.90; N, 13.62; S, 15.65 | 7.09 (1H, dd, J = 8.4, 5.7), 7.41 (1H, dd, J = 5.1, 3.0), 7.55 (1H, dd, J = 5.1, 1.5), 7.70 (1H, td, J = 8.4, 2.0), 8.07 (1H, J = 3.0, 1.5), 8.30 (1H, m), 8.37 (1H, d, J = 8.4) |
| Ib-131 | 258-260 | C13H9N3O2S | C, 57.55; H, 3.34; N, 15.49; S, 11.82 | C, 57.56; H, 3.40; N, 15.47; S, 11.59 | *2) 6.76 (1H, dd, J = 1.8, 3.6), 7.26 (1H, d, J = 3.6), 7.53-7.64 (2H, m), 7.65-7.74 (1H, m), 7.98 (1H, d, J = 1.8), 8.11-8.20 (2H, m), 13.24 (1H, br) |
| Ib-133 | 189-191 | C13H9N3O3 | C, 61.18; H, 3.55; N, 16.46 | C, 61.01; H, 3.47; H, 16.39 | *2) 6.80 (1H, dd, J = 1.8, 3.6), 7.30 (1H, d, J = 3.6), 7.52-7.62 (2H, m), 7.63-7.72 (1H, m), 7.98-8.09 (3H, m), 12.18 (1H, br) |
| Ib-137 | 126-127 | C15H11N3O1 | C, 72.28; H, 4.45N, 16.86 | C, 72.37; H, 4.38N, 16.17 | 7.57 (2H, d, J = 7.4), 7.60-7.89 (4H, m), 8.01 (2H, dd, J = 1.6, 8.1), 8.12 (1H, m), 8.76 (1H, br. s), 10.01 (1H, s) |

TABLE 24-continued

| | | | | | |
|---|---|---|---|---|---|
| Ib-144 | 226-228 | C15H10Cl1N3O1 | C, 63.50; H, 3.55 Cl, 12.49; N, 14.81 | C, 63.51; H, 3.76 Cl, 12.51; N, 14.60 | 7.53 (2H, d, J = 8.8), 7.66-7.88 (3H, m), 7.95 (2H, d, J = 8.8), 8.12 (1H, m), 8.71 (1H, br. s), 9.97 (1H, s) |
| Ic-1 | 126-127 | C16H15NO2 | C, 75.87; H, 5.97; N, 5.53 | C, 76.00; H, 5.89; N, 5.53 | 3.84 (3H, s), 6.13 (1H, d, J = 12.3), 6.90-7.47 (10H, m) |
| Ic-5 | 131.5-132.5 | C16H17NO2 | C, 75.27; H, 6.71; N, 5.49 | C, 75.21; H, 6.74; N, 5.53 | 2.63 (2H, t, J = 7.6), 3.05 (2H, t, J = 7.6), 3.78 (3H, s), 6.81-6.86 (2H, m), 6.95 (1H, brs), 7.21-7.34 (7H, m) |
| Id-1 | 159-161 | C16H14N2O | C, 76.78; H, 5.64; N, 11.19 | C, 76.86; H, 5.68; N, 11.23 | *1) 6.13 (1H, d, J = 14.7), 6.91-6.94 (2H, m), 7.03-7.07 (1H, m), 7.32-7.39 (3H, m), 7.46-7.60 (3H, m), 7.70-7.76 (1H, m), 8.26 (1H, br), 8.28-8.31 (1H, m), 8.34 (1H, d, J = 8.7) |

EXPERIMENT 1

Activity to Enhance the Expression of Human apoAI

The promoter region of the gene encoding human apoAI was isolated, and ligated upstream the structure gene of firefly luciferase to construct a reporter plasmid. The reporter plasmid and a marker plasmid conferring the neomycin resistance were co-infected to cell lines derived from human hepatoma, HepG2 cells, and the cell lines were incubated in a selection medium comprising DMEM medium containing 10% fetal calf serum supplemented with G418 (Final concentration: 0.7 mg/mL, Gibco) to give established strains that stably expressed the reporter molecule. The strains were seeded to a 96-well culture plates at a density of 50,000 cells per well, and incubated for 48 hours at 37° C. under an atmosphere of 5% carbon dioxide. Then, a solution of the compounds according to the invention in DMSO was added to the wells at final concentrations of 0 to 10 μg/mL. After further incubation for 24 hours, the cells were added with a luciferase assay reagent (Piccagene LT 7.5 registered trade mark, Toyo Ink, KK), and the luciferase activity was determined using a luminometer (MicroBeta™ TRILUX, 1 sec/well, Wallac). The concentration of the compounds, which intensified the luciferase activity twice compared to that of control (DMSO without any compound of the invention added) was set as the minimal effective dose (MED). The results are shown in Table 25.

TABLE 25

| | MED (μg/ml) |
|---|---|
| Ia-1 | 0.13 |
| Ia-3 | 0.49 |
| Ia-4 | 0.54 |
| Ia-6 | 0.34 |
| Ia-16 | 0.21 |
| Ia-17 | 0.5 |
| Ia-30 | 0.14 |
| Ia-39 | 0.1 |
| Ia-42 | 0.8 |
| Ia-44 | 0.18 |
| Ia-45 | 0.54 |
| Ia-46 | 0.17 |
| Ia-61 | 0.31 |
| Ia-64 | 0.13 |
| Ia-95 | 1.2 |
| Ia-105 | 0.68 |
| Ia-144 | 0.08 |
| Ia-145 | 0.44 |
| Ia-152 | 0.22 |
| Ia-153 | 0.19 |
| Ia-161 | 0.14 |
| Ib-4 | 0.31 |
| Ib-6 | 0.71 |
| Ib-7 | 0.39 |
| Ib-8 | 0.46 |

TABLE 25-continued

| | MED (μg/ml) |
|---|---|
| Ib-9 | 1.53 |
| Ib-11 | 0.28 |
| Ib-17 | 0.30 |
| Ib-18 | 0.22 |
| Ib-19 | 0.25 |
| Ib-20 | 0.81 |
| Ib-25 | 0.71 |
| Ib-26 | 0.33 |
| Ib-28 | 0.32 |
| Ib-35 | 0.21 |
| Ib-73 | 1.2 |
| Ib-105 | 0.81 |
| Ib-131 | 0.66 |
| Ib-137 | 0.72 |
| Ib-144 | 0.91 |
| Id-1 | 0.5 |

Table 25 shows that the compounds according to the invention can promote the function of the gene encoding human apoAI, thereby enhancing the expression of apoAI.

| Formulation 1 Tablets | |
|---|---|
| compound (Ia-1) | 15 mg |
| starch | 15 mg |
| lactose | 15 mg |
| crystalline cellulose | 19 mg |
| polyvinyl alcohol | 3 mg |
| distilled water | 30 mL |
| calcium stearate | 3 mg |

The ingredients other than calcium stearate were mixed uniformly, and the mixture was powdered, granulated, and dried to give granules having a suitable size. Then, the calcium stearate was added and the mixture was compressed to give a tablet formulation.

| Formulation 2 Capsules | |
|---|---|
| compound (Ia-7) | 10 mg |
| magnesium stearate | 10 mg |
| lactose | 80 mg |

The ingredients were homogeneously mixed to give powders or fine particles, which were formed into a powder formulation. This was filled in capsules to give a capsule formulation.

| Formulation 3 Granules | |
| --- | --- |
| compound (Ia-1) | 30 g |
| lactose | 265 g |
| magnesium stearate | 5 g |

The ingredients were mixed thoroughly, and the mixture was compressed, powdered, granulated and sieved to give a granule formulation.

INDUSTRIAL APPLICABILITY

As is apparent from the experiment as described above, the compounds according to the invention have an activity for enhancing the expression of apoAI. Thus, the compounds according to the invention are useful as pharmaceutical compositions for preventing and/or treating dyslipidemia or arteriosclerotic diseases, and in a method and use therefor.

The invention claimed is:

1. A method of enhancing the expression of apoAI, which comprises administering a therapeutically effective amount of a compound of formula (I):

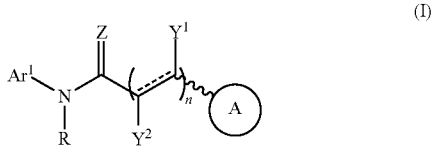

(I)

in which
ring A is $Ar^2$;
$Ar^1$ and $Ar^2$ are independently a monocyclic or bicyclic aromatic carbocyclic group that may be optionally substituted;
R is a hydrogen or a lower alkyl that may be optionally substituted;
Z is oxygen or sulfur;
$Y^1$ and $Y^2$ are independently a hydrogen, a halogen, a lower alkyl that may be optionally substituted, a carboxy, a lower alkoxycarbonyl that may be optionally substituted, a cyano, a phenyl that may be optionally substituted, or a monocyclic aromatic heterocyclic group that may be optionally substituted, and two $Y^1$s or more and two $Y^2$s or more each may be different among them;
n is an integer of 0 to 2;
the broken line is independently the presence or absence of a bond; and
the wavy line represents a cis- or trans-geometrical isomerism with respect to the double bond; or a pharmaceutically acceptable salt thereof to a patient expected to enhance the expression of apoAI.

2. The method according to claim 1, in which $Ar^1$ in formula (I) is phenyl that may be optionally substituted.

3. The method according to any one of claims 1 or 2, in which ring A in formula (I) is a phenyl that may be optionally substituted.

4. The method according to claim 3, in which ring A in formula (I) is a phenyl which may be optionally substituted, wherein the substituent is a halogen; a lower alkyl optionally substituted by a halogen or a lower alkoxy; a hydroxy; a lower alkoxy; phenoxy; naphtyloxy; an acyloxy; a carboxy; a lower alkoxycarbonyl; an amino optionally substituted by a lower alkyl or a lower acyl; a phenyl that may be optionally substituted by a lower alkoxy; a nitro; a lower alkylthio; a cyano; a monocyclic heterocyclic group; or an alkylenedioxy.

5. The method according to any one of claims 1 or 2, in which n in formula (I) is 1 or 2, and $Y^1$ and/or $Y^2$ in formula (I) is a hydrogen.

6. The method according to any one of claims 1 or 2, in which Z in formula (I) is oxygen.

7. The method according to any one of claims 1 or 2, in which n in formula (I) is 1 or 2, and all of the broken line are the presence of a bond.

8. The method according to claim 7, in which when n is 1 and the broken line is the presence of a bond, then the wavy line represents trans configuration with respect to the relationship between NRCZ and ring A, or alternatively when n is 2 and the broken lines are the presence of a bond, then the wavy line represents trans configuration with respect to the relationship between NRCZ and $CY^2$ and/or the relationship between $CY^1$ and ring A.

9. A method of treatment of dyslipidemia or arteriosclerotic diseases, which comprises administrating a therapeutically effective amount of a compound of formula (I) as defined in claim 1, or a pharmaceutically acceptable salt thereof to a patient suspected to have dyslipidemia or arteriosclerotic diseases.

10. The method according to claim 3, in which $Y^1$ and/or $Y^2$ in formula (I) is a hydrogen.

11. The method according to claim 4, in which $Y^1$ and/or $Y^2$ in formula (I) is a hydrogen.

12. The method according to claim 3, in which Z in formula (I) is oxygen.

13. The method according to claim 4, in which Z in formula (I) is oxygen.

14. The method according to claim 5, in which Z in formula (I) is oxygen.

15. The method according to claim 3, in which n in formula (I) is 1 or 2, and all of the broken line are the presence of a bond.

16. The method according to claim 4, in which n in formula (I) is 1 or 2, and all of the broken line are the presence of a bond.

17. The method according to claim 5, in which n in formula (I) is 1 or 2, and all of the broken line are the presence of a bond.

18. The method according to claim 6, in which n in formula (I) is 1 or 2, and all of the broken line are the presence of a bond.

19. The method according to claim 1, in which n in formula (I) is 0.

* * * * *